US012788716B2

(12) United States Patent
Perry et al.

(10) Patent No.: US 12,788,716 B2
(45) Date of Patent: Nov. 10, 2026

(54) METHODS OF TREATING FUNGAL INFECTIONS

(71) Applicant: CIPLA TECHNOLOGIES LLC, Hauppauge, NY (US)

(72) Inventors: Jason M. Perry, Cambridge, MA (US); David L. Hava, Natick, MA (US); Aidan Curran, Duxbury, MA (US)

(73) Assignee: CIPLA TECHNOLOGIES LLC, Hauppauge, NY (US)

( * ) Notice: Subject to any disclaimer, the term of this patent is extended or adjusted under 35 U.S.C. 154(b) by 0 days.

(21) Appl. No.: 17/047,585

(22) PCT Filed: Apr. 18, 2019

(86) PCT No.: PCT/US2019/028112
§ 371 (c)(1),
(2) Date: Oct. 14, 2020

(87) PCT Pub. No.: WO2019/204597
PCT Pub. Date: Oct. 24, 2019

(65) Prior Publication Data

US 2021/0113461 A1 Apr. 22, 2021

Related U.S. Application Data

(60) Provisional application No. 62/659,601, filed on Apr. 18, 2018, provisional application No. 62/696,510, filed on Jul. 11, 2018.

(51) Int. Cl.

| | |
|---|---|
| ***A61K 9/00*** | (2006.01) |
| ***A61K 9/08*** | (2006.01) |
| ***A61K 9/10*** | (2006.01) |
| ***A61K 31/496*** | (2006.01) |
| ***A61P 31/10*** | (2006.01) |

(52) U.S. Cl.
CPC .......... *A61K 9/0075* (2013.01); *A61K 31/496* (2013.01); *A61P 31/10* (2018.01)

(58) Field of Classification Search
CPC .. A61K 9/0075; A61K 31/496; A61K 9/0073; A61K 47/26; A61P 11/00
See application file for complete search history.

(56) References Cited

U.S. PATENT DOCUMENTS

| | | | | |
|---|---|---|---|---|
| 4,069,819 | A | 1/1978 | Valentini et al. | |
| 4,916,134 | A | 4/1990 | Heeres et al. | |
| 4,995,385 | A | 2/1991 | Valentini et al. | |
| 11,116,722 | B2 * | 9/2021 | Perry | A61K 9/145 |
| 2011/0190245 | A1 * | 8/2011 | Rundfeldt | A61K 31/4174 241/15 |
| 2015/0004233 | A1 * | 1/2015 | Lipp | A61K 39/3955 424/152.1 |
| 2015/0136130 | A1 * | 5/2015 | DeHaan | A61K 31/56 53/473 |
| 2021/0145739 | A1 * | 5/2021 | Perry | A61K 9/145 |

FOREIGN PATENT DOCUMENTS

| | | | |
|---|---|---|---|
| CN | 106900172 | A | 6/2017 |
| CN | 109996536 | A | 7/2019 |
| MX | 2019004322 | A | 12/2019 |
| WO | 2006026502 | A1 | 3/2006 |
| WO | 2009106333 | A1 | 9/2009 |
| WO | 20170127641 | A1 | 7/2017 |
| WO | 2018071757 | A1 | 4/2018 |
| WO | 2019204597 | A1 | 10/2019 |

OTHER PUBLICATIONS

Pilcer et al, Formulations strategy and use of excipients in pulmonary drug delivery; International Journal of Pharmaceutics 392 (2010) 1-19 (Year: 2010).*
Foreign Communication from a Related Application—International Search Report and Written Opinion of International Application No. PCT/US2019/028112, dated Jul. 23, 2019, 14 pages.
Foreign communication from related application—International Preliminary Report on Patentability of International Application No. PCT/US2019/028112, dated Oct. 20, 2020, 9 pages.
Broeders, M.E.A.C., et al., "Peak inspiratory flow rate and slope of the inhalation profiles in dry powder inhalers", European Respiratory Journal, 2001, pp. 780-783, vol. 18, ERS Journals Ltd.
Chrystyn, H., "The Diskus (TM): a review of its position among dry powder inhaler devices", International Journal of Clinical Practice, 2006, pp. 1022-1036, vol. 61, No. 6, Blackwell Publishing Ltd.
Curran, A.K., et al., "Efficacy of PUR1900, an Inhaled Antifungal Therapy, in a Guinea Pig Model of Invasive Pulmonary Aspergillosis", Feb. 2018, Pulmatrix, Inc., Lexington, Massachusetts, USA.
Curran, A.K., et al., "Systemic and Pulmonary Exposure of PUR1900 Following Inhalation Dosing in Rats and Dogs Over 28 Days", Nov. 2017, Pulmatrix, Inc., Lexington, Massachusetts, USA.
Duret, Christophe, et al., "Pharmacokinetic evaluation in mice of amorphous itraconazole-based dry powder formulations for inhalation with high bioavailability and extended lung retention", European Journal of Pharmaceutics and Biopharmaceutics, 2014, pp. 46-54, vol. 86, Elsevier Science Publishers B.V.
Hava, David L., "Advances in Pulmonary Delivery of Inhaled Anti-Infectives", Pulmatrix, Drugdelivery.com, 2016, pp. 14-19, vol. 2016, No. 66, Frederick Furness Publishing Ltd.
Islam, Nazrul, et al.,"Dry powder inhalers (DPIs)—A review of device reliability and innovation", International Journal of Pharmaceutics, 2008, pp. 1-11, vol. 360, Elsevier B.V.
Masters, Keith, Spray Drying Handbook, 1985, 4th Edition, Halsted Press, 1 page of cover and publishing Information, John Wiley & Sons, New York.

(Continued)

*Primary Examiner* — Mina Haghighatian
(74) *Attorney, Agent, or Firm* — Conley Rose, P.C.; Rodney B. Carroll

(57) ABSTRACT

The invention relates to methods of treating fungal infections by administering to the respiratory tract of a patient in need thereof an effective amount of an anti-fungal agent, preferably itraconazole, wherein said anti-fungal agent is administered in an amount sufficient to concurrently achieve a) a lung concentration of anti-fungal agent of at least 500 ng/g or ng/mL and b) a plasma concentration of anti-fungal agent of no more than 25 ng/mL. The preferred form is as dry powder inhalation.

20 Claims, 5 Drawing Sheets

(56) References Cited

OTHER PUBLICATIONS

Shetty Advait, et al., "Advancements in Dry Powder Inhaler", Asian Journal of Pharmaceutical and Clinical Research, 2017, pp. 8-12, vol. 10, No. 2, Innovare Academic Sciences Pvt Ltd.

Steckel, Hartwig, et al., "In vitro evaluation of dry powder inhalers I: drug deposition of commonly used devices", International Journal of Pharmaceutics, 1997, pp. 19-29, vol. 154, Elsevier Science B.V.

Sung, Jean C., et al., "iSperse (TM): Formulation and In Vitro Characterization of a Novel Dry Powder Drug Delivery Technology", Respiratory Drug Delivery Europe 2011, pp. 411-414, Pulmatrix Inc.

Tiddens, H.A., et al., "Effect of Dry Powder Inhaler Resistance on the Inspiratory Flow Rates and Volumes of Cystic Fibrosis Patients of Six Years and Older", Journal of Aerosol Medicine, 2006, pp. 456-465, vol. 19, No. 4, Mary Ann Liebert, Inc.

Vaughn, Jason. M., et al., "Single dose and multiple dose studies of itraconazole nanoparticles", European Journal pf Pharmaceutics and Biopharmaceutics, 2006, pp. 95-102, vol. 63, No. 2, Elsevier B.V.

Yang, Wei., et al., "Comparison of bioavailability of amorphous versus crystalline itraconazole nanoparticles via pulmonary administration in rats", European Journal of Pharmaceutics and Biopharmaceutics, 2010, pp. 33-41, vol. 75, Elsevier B.V.

"<601>Aerosols, Nasal Sprays, Metered-Dose Inhalers, and Dry Powder Inhalers", USP 35, Dec. 1, 2012, pp. 232-252, The United States Pharmacopeial Convention.

Priority document as submitted to the International Bureau—U.S. Appl. No. 62/659,601, entitled "Methods of Treating Fungal Infections", filed Apr. 18, 2018, 78 pages including cover.

Priority document as submitted to the International Bureau—U.S. Appl. No. 62/696,510, entitled "Methods of Treating Fungal Infections", filed Jul. 11, 2018, 88 pages including cover.

"Safety, Tolerability and Pharmacokinetics of PUR1900 (Itraconazole Powder) in Healthy Volunteers and Adults With Asthma", Clinical Trial Identifier NCT03479411, Mar. 20, 2018, 9 pages, Pulmatrix, Inc., https://clinicaltrials.gov/ct2/show/NCT03479411.

Foreign Communication from Related Application—European Office Action, regarding Application No. EP 19721501.5-1112, dated Dec. 16, 2022, 7 pages.

Foreign Communication from Related Application—Mexican Office Action, regarding Application No. MX/2022/080559 , dated Nov. 24, 2022, 6 pages.

Foreign Communication from Related Application—Russian Office Action, regarding Application No. RU 2020136407/14 , dated Dec. 1, 2022, 11 pages.

Foreign Communication from Related Application—Japanese Office Action, regarding Application No. JP 2021-506374 dated Apr. 18, 2023 8 pages.

Foreign Communication from Related Application—Mexican Office Action, regarding Application No. MX/2020/010977, dated Apr. 20, 2023 10 pages.

Foreign Communication from Related Application—Chinese Office Action, regarding Application No. CN 201980040027.4 , dated Mar. 20, 2023 19 pages.

Foreign Communication from Related Application—Australian Office Action, regarding Application No. AU 2019256453 dated May 20, 2024, 9 pages.

Foreign Communication from Related Application—Israeli Office Action, regarding Application No. IL 135-043, dated Apr. 25, 2023, 9 pages.

Duret, C., et al., "New inhalation-optimized itraconazole nanoparticle-based dry powders for the treatment of invasive pulmonary aspergillosis", International Journal of Nanomedicine, vol. 2012:7, 5475-5489, DOI: 10.2147/IJN.S34091, 2012.

Merlos, R., et al., "Optimization and scaling-up of ITZ-based dry powders for inhalation", Journal of Drug Delivery Science and Technology, vol. 37, pp. 147-157, doi:https://doi.org/10.1016/j.jddst.2016.12.009, 2017.

Foreign Communication from Related Application—Canadian Office Action, regarding Application No. CA 3,097,419 dated Jul. 10, 2025, 7 pages.

Foreign Communication from Related Application—European Examination Report, regarding Application No. EP 19721501.5-1109, dated Mar. 14, 2025, 6 pages.

Foreign Communication from Related Application—Brazilian Office Action, regarding Application No. BR112020021154-0, dated Oct. 27, 2025, 6 pages with English translation.

Foreign Communication from Related Application—New Zealand, Examination Report, regarding Application No. NZ 769830 dated Jun. 24, 2026, 5 pages.

Safety, Tolerability and Pharmacokinetics of PUR 1900 (Itraconazole Powder) in Healthy Volunteers and Adults With Asthma, NCT03479411, [retrieved from internet on Jun. 18, 2026]. Retrieved from <https://clinicaltrials.gov/study/NCT03479411?tab=history&a=1#version-content-panel>.

Foreign Communication from Related Application - Canadian Office Action, regarding Application No. CA 3,097,419 dated Jul. 8, 2026, 5 pages.

* cited by examiner

Kinetics of Formulation XIX, Formulation XII and Sporanox

Over 7 Days of dosing

Kinetics of Formulation XIX, Formulation XII and Sporanox

Over 7 Days of dosing

Single Dose PUR1900 Plasma Pharmacokinetic Profile Over 96 Hours in Healthy Volunteers

Pharmacokinetic Profile of Itraconazole in (A) Sputum and (B) Plasma Following Single Doses of PUR1900 (▲) or Oral Sporanox (△) Administered to Asthmatics

METHODS OF TREATING FUNGAL INFECTIONS

RELATED APPLICATIONS

This application is a filing under 35 U.S.C. 371 as the National Stage of International Application No. PCT/US2019/028112, filed Apr. 18, 2019 and entitled "Methods of Treating Fungal Infections", which claims the benefit of U.S. Patent Application No. 62/659,601, filed on Apr. 18, 2018, and U.S. Patent Application No. 62/696,510, filed on Jul. 11, 2018, the entire contents of each of which are incorporated herein by reference.

BACKGROUND

Pulmonary fungal infections by *Aspergillus* spp. and other fungi are a growing concern in patients with decreased respiratory function, such as cystic fibrosis (CF) patients. For example, patients can have chronic pulmonary fungal infection or Allergic Bronchopulmonary Aspergillosis (ABPA), a severe inflammatory condition that is typically treated with a long course of oral steroids. *A. fumigatus* is the predominant species causing disease, however other species such as *A. niger, A. terrus, A. flavus* infect humans as well. Pulmonary *A. fumigatus* infections manifest as a range of diseases depending on the host immune state and underlying lung disease. In immunocompromised hosts, invasive pulmonary aspergillosis (IPA) is a life-threatening disease occurring in patients with impaired immunity as a result of treatment for hematological cancers, organ transplantation or other immunosuppressive conditions.

The mortality rate of IPA in neutropenic and hematopoietic stem-cell transplant recipients are >50% and >90%, respectively. Because of the significant mortality associated with IPA, antifungal prophylaxis is used to reduce the risk of infection. *A. fumigatus* also causes chronic infection in patients with chronic lung disease such as asthma and cystic fibrosis (CF). In asthmatics, fungal colonization and infection can result in allergic bronchopulmonary aspergillosis (ABPA). ABPA is a complex hypersensitivity reaction that occurs in the response to colonization of the airways with *Aspergillus fumigatus*, typically in patients with asthma or CF. The immunological response to fungal antigens in the airway results in T-helper type 2 (Th2) cell activation and inflammatory cell recruitment to the airways, the most significant of which are eosinophils. Expression of interleukin-4 and interleukin-5 (IL-4 and IL-5) is central to these processes. IL-4 stimulates the upregulation of adhesion molecules involved in eosinophil recruitment and the production of immunoglobulin E (IgE) by B cells, which in turn leads to mast cell activation. IL-5 produced by both Th2 cells and mast cells is a key mediator of eosinophil activation. Activation of both mast cells and eosinophils results in the release of mediators that induce bronchoconstriction.

A number of anti-fungal agents are known including triazoles (e.g., itraconazole), polyenes (e.g., amphotericin B), and echinocandins. Anti-fungal agents typically have low aqueous solubility and poor oral bioavailability and obtaining pharmaceutical formulations that can be administered to provide safe and therapeutic levels of anti-fungal agents has been challenging. Anti-fungal agents are typically administered as oral or intravenous (IV) formulations as treatments for fungal infections, including pulmonary infection and ABPA. However, such formulations are limited by poor oral bioavailability, adverse side effects and toxicity, and extensive drug-drug interactions. Alternative approaches, such as delivery to the airway by inhalation, which theoretically could reduce systemic side effects also present challenges. Notably, it is well known that agents with poor aqueous solubility produce local lung toxicity (e.g., local inflammation, granuloma) when inhaled. The conventional approach to address local toxicity of poorly soluble agents is to formulate the agent to increase its rate of dissolution, for example using amorphous formulations.

The chemical structure of itraconazole is described in U.S. Pat. No. 4,916,134. Itraconazole is a triazole anti-fungal agent providing therapeutic benefits (e.g., in the treatment of fungal infections), and is the active ingredient in SPORANOX® (itraconazole; Janssen Pharmaceuticals) which may be delivered orally or intravenously. Itraconazole can be synthesized using a variety of methods that are well known in the art. Although itraconazole is not FDA-approved for the treatment of ABPA in asthma patients, it is considered to be a "standard of care" therapy. The oral capsule formulation of Sporanox has a labeled indication for the treatment of aspergillosis, pulmonary and extrapulmonary, in patients who are intolerant of or who are refractory to amphotericin B therapy. Oral itraconazole is however considered to be a "standard of care" therapy for the treatment of ABPA. While itraconazole is the only antifungal with proven efficacy based on randomized controlled trials in treating ABPA, oral doses of itraconazole have variable absorption and food interactions, and present a poor relationship between serum and sputum levels. High plasma concentrations of itraconazole can lead to significant drug-drug interactions (DDI) through inhibition of CYP3A4 in the liver. The poor pharmacokinetic and side effect profile of oral itraconazole limits its therapeutic efficacy.

A need exists for new methods of administering formulations of anti-fungal agents that can be administered to achieve a significantly higher lung:plasma ratio by oral inhalation administration when compared to oral solution administration to treat fungal infections, thereby reducing systemic effects.

SUMMARY OF THE INVENTION

The invention relates to methods of treating a patient by administering dry powder formulations comprising homogenous respirable dry particles that contain 1) an anti-fungal agent in crystalline particulate form, 2) a stabilizer, and optionally 3) one or more excipients, with an amount of dry powder formulation sufficient to maintain steady state concentration. One advantage of the present invention over the prior art is the methods allow for administration of a dry powder formulation that achieves a high lung concentration, while keeping the plasma concentration low, thereby reducing systemic effects of the anti-fungal active ingredient. In one particular aspect, the anti-fungal agent in crystalline particulate form is not a polyene anti-fungal agent. In another particular aspect, the invention relates to 1) a triazole anti-fungal agent in crystalline particulate form, 2) a stabilizer, and optionally 3) one or more excipients. In a more particular aspect, the triazole anti-fungal agent is itraconazole.

In one aspect, the invention relates to a method for treating a fungal infection comprising administering to the respiratory tract of a patient in need thereof an effective amount of an anti-fungal agent, wherein said anti-fungal agent is administered in an amount sufficient to concurrently achieve a) a lung concentration of anti-fungal agent of at least 500 ng/g or ng/mL and b) a plasma concentration of anti-fungal agent of no more than 25 ng/mL.

In another aspect, the invention relates to a method for treating aspergillosis comprising administering to the respiratory tract of a patient in need thereof an effective amount of an anti-fungal agent, wherein said anti-fungal agent is administered in an amount sufficient to concurrently achieve a) a lung concentration of anti-fungal agent of at least 500 ng/g or ng/mL and b) a plasma concentration of anti-fungal agent of no more than 25 ng/mL.

In another aspect, the invention relates to a method for treating allergic bronchopulmonary aspergillosis (ABPA) comprising administering to the respiratory tract of a patient in need thereof an effective amount of an anti-fungal agent, wherein said anti-fungal agent is administered in an amount sufficient to concurrently achieve a) a lung concentration of anti-fungal agent of at least 500 ng/g or ng/mL and b) a plasma concentration of anti-fungal agent of no more than 25 ng/mL.

In a further aspect, the invention relates to a method for treating or reducing the incidence or severity of an acute exacerbation of a respiratory disease comprising administering to the respiratory tract of a patient in need thereof an effective amount of an anti-fungal agent, wherein said anti-fungal agent is administered in an amount sufficient to concurrently achieve a) a lung concentration of anti-fungal agent of at least 500 ng/g or ng/mL and b) a plasma concentration of anti-fungal agent of no more than 25 ng/mL.

The lung and plasma concentrations may persist for at least about 24 hours following administration of a single dose of anti-fungal agent.

The lung and plasma concentrations can be steady state concentrations.

The anti-fungal agent may be administered in the form of a dry powder or a liquid formulation.

In another aspect, the invention relates to a method for treating a fungal infection comprising administering to the respiratory tract of a patient in need thereof an effective amount of an anti-fungal agent, wherein said anti-fungal agent is administered in a single dose or in an initial dose followed by one or more subsequent doses, wherein a lung:plasma ratio of at least 100:1 is achieved.

In another aspect, the invention relates to a method for treating aspergillosis comprising administering to the respiratory tract of a patient in need thereof an effective amount of an anti-fungal agent, wherein said anti-fungal agent is administered in a single dose or in an initial dose followed by one or more subsequent doses, wherein a lung:plasma ratio of at least 100:1 is achieved.

In another aspect, the invention relates to a method for treating allergic bronchopulmonary aspergillosis (ABPA) comprising administering to the respiratory tract of a patient in need thereof an effective amount of an anti-fungal agent, wherein said anti-fungal agent is administered in a single dose or in an initial dose followed by one or more subsequent doses, wherein a lung:plasma ratio of at least 100:1 is achieved.

In another aspect, the invention relates to a method for treating or reducing the incidence or severity of an acute exacerbation of a respiratory disease comprising administering to the respiratory tract of a patient in need thereof an effective amount of an anti-fungal agent, wherein said anti-fungal agent is administered in a single dose or in an initial dose followed by one or more subsequent doses, wherein a lung:plasma ratio of at least 100:1 is achieved.

The patient may have cystic fibrosis. The patient may have asthma.

In another aspect, the invention relates to a method of treating a fungal infection in an immunocompromised patient comprising administering to the respiratory tract of a patient in need thereof an effective amount of an anti-fungal agent, wherein said anti-fungal agent is administered in an amount sufficient to achieve a) a lung concentration of anti-fungal agent of at least 500 ng/g or ng/mL and b) a plasma concentration of anti-fungal agent of no more than 25 ng/mL.

In another aspect, the invention relates to a method for treating a fungal infection in an immunocompromised patient comprising administering to the respiratory tract of a patient in need thereof an effective amount of an anti-fungal agent, wherein said anti-fungal agent is administered in a single dose or in an initial dose followed by one or more subsequent doses, wherein a lung:plasma ratio of at least 100:1 is achieved.

The invention also relates to a method of treating a fungal infection comprising administering to the respiratory tract of a patient in need thereof an initial one or more fungicidal dose(s) of a dry powder formulation that contains anti-fungal agents until steady state is achieved, followed by one or more fungistatic dose(s) to maintain steady state to a patient in need thereof. The fungistatic dose may be administered less frequently than the fungicidal dose was administered. The fungistatic dose may be less than the fungicidal dose. Each of the doses may independently comprise about 2 to about 35 mg nominal dose of anti-fungal active ingredient. The interval between doses may be at least about 1 day. The interval between doses may be at least about 2 days. The interval between doses may be at least about 3 days. The number of doses administered per week may be about 3 doses.

In one aspect, the invention relates to a method for treating a fungal infection, comprising administering to the respiratory tract of a patient in need thereof an effective amount of an anti-fungal agent, wherein said anti-fungal agent is administered to achieve steady state anti-fungal concentration in the lung, and then administering the anti-fungal in one or more doses wherein each dose contains an amount of anti-fungal agent sufficient to achieve a) a lung concentration of anti-fungal agent of at least about 500 ng/g or ng/mL for at least about 24 hours and b) a plasma concentration of anti-fungal agent of no more than about 25 ng/mL for at least 24 hours.

The invention also relates to a method for treating a fungal infection with itraconazole, comprising administering itraconazole to the respiratory tract of a patient in need thereof, wherein one or more fungicidal doses of itraconazole are administered, followed by administration of one or more fungistatic doses, and wherein the fungicidal and fungistatic doses do not produce a plasma concentration of itraconazole that is higher than 25 ng/mL.

In another aspect, the invention relates to a method for treating a fungal infection with itraconazole, comprising i) administering itraconazole to the respiratory tract of a patient in need thereof in an amount sufficient to achieve a fungicidal level of itraconazole in the lung, ii) determining whether the plasma concentration of itraconazole is 25 ng/mL or higher, and iii) if the plasma concentration of itraconazole is 25 ng/mL or higher, reducing the amount of itraconazole administered to the patient to an amount sufficient to achieve a fungistatic level of itraconazole in the lung; wherein risk of systemic effects of itraconazole are reduced.

In another aspect, the invention relates to a method of treating a fungal infection comprising administering to the respiratory tract of a patient in need thereof one or more dose(s) of an anti-fungal agent to achieve a fungicidal level of anti-fungal agent in the lung, followed by one or more dose(s) to maintain a fungistatic level of anti-fungal agent in the lung. The dose of anti-fungal agent to achieve a fungicidal level of anti-fungal agent in the lung may be administered less frequently than the dose(s) to maintain a fungistatic level of anti-fungal agent in the lung. The dose to achieve a fungicidal level of anti-fungal agent in the lung may be less than the dose to maintain a fungistatic level of anti-fungal agent in the lung.

In another aspect, the invention relates to a method of treating a fungal infection comprising administering to the respiratory tract of a patient in need thereof one or more loading dose(s) of an anti-fungal agent to achieve a minimum fungicidal concentration (MFC90) in the lung for at least 24 hours, followed by one or more maintenance doses to achieve a minimum inhibitory concentration (MIC90) in the lung for at least 24 hours. The MFC90 may be at least 2000 ng/g or ng/mL. The MIC90 may be at least 500 ng/g or ng/mL. The maintenance dose may be administered less frequently than the fungicidal dose was administered. The maintenance dose may be less than the loading dose.

DETAILED DESCRIPTION OF THE INVENTION

Figure 1A:
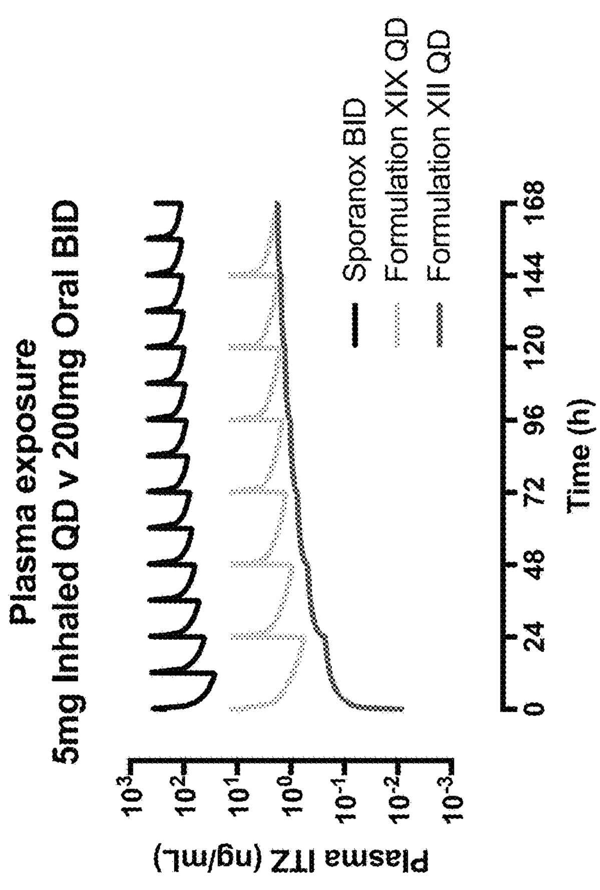
FIGS. 1A and 1B are graphs showing the simulated kinetics of Formulation XIX, Formulation XII, and Sporanox in terms of Plasma Exposure (FIG. 1A) and Lung Exposure (FIG. 1B) using a model established from animal PK data and human data for Sporanox. In both simulations 5 mg was inhaled once daily (Formulations XIX and XII), while 200 mg Sporanox oral solution dose was administered twice a day. The concentration of itraconazole was measured over seven days of dosing.

This disclosure relates to methods of treating a patient having a respiratory disease by administering an amount of respirable dry powder that contains an anti-fungal agent in crystalline particulate form sufficient to achieve steady state concentration. The inventors have discovered that administration of a nominal dose of 5 mg or greater of an anti-fungal in crystalline particulate form in a dry powder formulation achieves a fungicidal concentration instead of just a fungistatic concentration. Thus, this disclosure also relates to a dosage regimen comprising an initial one or more dose(s) comprising fungicidal doses of a dry powder formulation that contains anti-fungal agents, such as itraconazole, that is continued until steady state is reached, followed by a fungistatic course (e.g., lower doses or less frequent doses) to maintain steady state.

The dry powders may be administered to a patient by inhalation, such as oral inhalation. To achieve oral inhalation, a dry powder inhaler may be used, such as a passive dry powder inhaler. The dry powder formulations can be used to treat or prevent fungal infections in a patient, such as *aspergillus* infections. Patients that would benefit from the dry powders are, for example, those who suffer from cystic fibrosis, asthma, and/or who are at high risk of developing fungal infections due to being severely immunocompromised. An inhaled formulation of anti-fungal agent (e.g., itraconazole) minimizes many of the downsides of oral or intravenous (IV) formulations in treating these patients.

Surprisingly, dry powder formulations that contain anti-fungal agents, such as itraconazole, in amorphous form have shorter lung residence times, reduced lung to plasma exposure ratios and undesirable toxic effects on lung tissue when inhaled at therapeutic doses. Without wishing to be bound by any particular theory, it is believed that the crystalline forms (e.g., nanocrystalline forms) of the material have a slower dissolution rate in the lung, providing more continuous exposure over a 24 hour period after administration and minimizing systemic exposure. In addition, the observed local toxicity in lung tissue with amorphous dosing is not related to the total exposure of the lung tissue to the drug, in terms of total dose or duration of exposure. Itraconazole has no known activity against human or animal lung cells and so increasing local concentration has no local pharmacological activity to explain the local toxicity. Instead, the toxicity of the amorphous form appears related to the increased solubility secondary to the amorphous nature of the itraconazole, resulting in supersaturation of the drug in the interstitial space and the resultant recrystallization in the tissue leading to local, granulomatous inflammation. Surprisingly, the inventors discovered that dry powders that contain anti-fungal agents in crystalline particulate form are less toxic to lung tissue. This was surprising because the crystalline particulate anti-fungal agents have a lower dissolution rate in comparison to the amorphous forms, and remain in the lung longer than a corresponding dose of the anti-fungal agent in amorphous form. Furthermore, the crystalline particulate anti-fungal agents also result in higher lung exposure after a single dose and over 28 days than a corresponding dose of the anti-fungal agent in amorphous form.

The crystallinity of the anti-fungal agent, as well as the size of the anti-fungal crystalline particles, appears to be important for effective therapy and for reduced toxicity in the lung. Without wishing to be bound by any particular theory, it is believed that smaller crystalline particles of the anti-fungal agent (e.g., nano-crystalline or micro-crystalline anti-fungal agent) will dissolve in the airway lining fluid more rapidly than larger crystalline particles—in part due to the larger total amount of surface area. It is also believed that crystalline anti-fungal agent will dissolve more slowly in the airway lining fluid than the amorphous anti-fungal agent. Accordingly, the dry powders described herein can be formulated using anti-fungal agents in crystalline particulate form that provide for a desired degree of crystallinity and particle size, and can be tailored to achieve desired pharmacokinetic properties while avoiding unacceptable toxicity in the lungs.

The respirable dry powders include homogenous respirable dry particles that contain 1) an anti-fungal agent in crystalline particulate form, 2) a stabilizer, and optionally 3) one or more excipients. Accordingly, the dry powders are characterized by respirable dry particles that contain a stabilizer, optionally one or more excipients, and a sub-particle (particle that is smaller than the respirable dry particle) that comprise crystalline anti-fungal agent. Such respirable dry particles can be prepared using any suitable method, such as by preparing a feedstock in which an anti-fungal agent in crystalline particulate form is suspended in an aqueous solution of excipients, and spray drying the feedstock.

Definitions

As used herein, the term "about" refers to a relative range of plus or minus 5% of a stated value, e.g., "about 20 mg" would be "20 mg plus or minus 1 mg".

As used herein, the terms "administration" or "administering" of respirable dry particles refers to introducing respirable dry particles to the respiratory tract of a subject.

As used herein, the term "amorphous" indicates lack of significant crystallinity when analyzed via powder X-ray diffraction (XRD).

As used herein, the term "fungicidal dose" refers to an amount of an anti-fungal agent needed to kill fungus (e.g., MFC50, MFC90). The fungicidal dose will vary depending on the specific type of fungal infection, and additional variability will depend on different factors that can be determined by a skilled physician.

As used herein, the term "fungistatic dose" refers to an amount of an anti-fungal agent needed to inhibit growth of a fungus (e.g., MIC50, MIC90). The fungistatic dose will vary depending on the specific type of fungal infection, and additional variability will depend on different factors that can be determined by a skilled physician.

The term "capsule emitted powder mass" or "CEPM" as used herein refers to the amount of dry powder formulation emitted from a capsule or dose unit container during an inhalation maneuver. CEPM is measured gravimetrically, typically by weighing a capsule before and after the inhalation maneuver to determine the mass of powder formulation removed. CEPM can be expressed either as the mass of powder removed, in milligrams, or as a percentage of the initial filled powder mass in the capsule prior to the inhalation maneuver.

The term "crystalline particulate form" as used herein refers to an anti-fungal agent (including pharmaceutically acceptable forms thereof including salts, hydrates, enantiomers as the like), that is in the form of a particle (i.e., sub-particle that is smaller than the respirable dry particles that comprise the dry powders disclosed herein) and in which the anti-fungal agent is at least about 50% crystalline. The percent crystallinity of an anti-fungal agent refers to the percentage of the compound that is in crystalline form relative to the total amount of compound present in the sub-particle. If desired, the anti-fungal agent can be at least about 60%, at least about 70%, at least about 80%, at least about 90%, at least about 95%, or about 100% crystalline. An anti-fungal agent in crystalline particulate form is in the form of a particle that is about 50 nanometers (nm) to about 5,000 nm volume median diameter (Dv50), preferably 80 nm to 1750 nm Dv50, or preferably 50 nm to 800 nm Dv50.

The term "dispersible" is a term of art that describes the characteristic of a dry powder or respirable dry particles to be dispelled into a respirable aerosol. Dispersibility of a dry powder or respirable dry particles is expressed herein, in one aspect, as the quotient of the volumetric median geometric diameter (VMGD) measured at a dispersion (i.e., regulator) pressure of 1 bar divided by the VMGD measured at a dispersion (i.e., regulator) pressure of 4 bar, or VMGD at 0.5 bar divided by the VMGD at 4 bar as measured by laser diffraction, such as with a HELOS/RODOS. These quotients are referred to herein as "1 bar/4 bar dispersibility ratio" and "0.5 bar/4 bar dispersibility ratio", respectively, and dispersibility correlates with a low quotient. For example, 1 bar/4 bar dispersibility ratio refers to the VMGD of a dry powder or respirable dry particles emitted from the orifice of a RODOS dry powder disperser (or equivalent technique) at about 1 bar, as measured by a HELOS or other laser diffraction system, divided by the VMGD of the same dry powder or respirable dry particles measured at 4 bar by HELOS/RODOS. Thus, a highly dispersible dry powder or respirable dry particles will have a 1 bar/4 bar dispersibility ratio or 0.5 bar/4 bar dispersibility ratio that is close to 1.0. Highly dispersible powders have a low tendency to agglomerate, aggregate or clump together and/or, if agglomerated, aggregated or clumped together, are easily dispersed or de-agglomerated as they emit from an inhaler and are breathed in by a subject. In another aspect, dispersibility is assessed by measuring the particle size emitted from an inhaler as a function of flowrate. As the flow rate through the inhaler decreases, the amount of energy in the airflow available to be transferred to the powder to disperse it decreases. A highly dispersible powder will have a size distribution such as is characterized aerodynamically by its mass median aerodynamic diameter (MMAD) or geometrically by its VMGD that does not substantially increase over a range of flow rates typical of inhalation by humans, such as about 15 to about 60 liters per minute (LPM), about 20 to about 60 LPM, or about 30 LPM to about 60 LPM. A highly dispersible powder will also have an emitted powder mass or dose, or a capsule emitted powder mass or dose, of about 80% or greater even at the lower inhalation flow rates. VMGD may also be called the volume median diameter (VMD), x50, or Dv50.

The term "dry particles" as used herein refers to respirable particles that may contain up to about 15% total of water and/or another solvent. Preferably, the dry particles contain water and/or another solvent up to about 10% total, up to about 5% total, up to about 1% total, or between 0.01% and 1% total, by weight of the dry particles, or can be substantially free of water and/or other solvent.

The term "dry powder" as used herein refers to compositions that comprise respirable dry particles. A dry powder may contain up to about 15% total of water and/or another solvent. Preferably the dry powder contain water and/or another solvent up to about 10% total, up to about 5% total, up to about 1% total, or between 0.01% and 1% total, by weight of the dry powder, or can be substantially free of water and/or other solvent. In one aspect, the dry powder is a respirable dry powder.

The term "effective amount," as used herein, refers to the amount of agent needed to achieve the desired effect; such as treating a fungal infection, e.g., an *aspergillus* infection, in the respiratory tract of a patient, e.g., a Cystic Fibrosis (CF) patient, an asthma patient and an immunocompromised patient; treating allergic bronchopulmonary aspergillosis (ABPA); and treating or reducing the incidence or severity of an acute exacerbation of a respiratory disease. The actual effective amount for a particular use can vary according to the particular dry powder or respirable dry particle, the mode of administration, and the age, weight, general health of the subject, and severity of the symptoms or condition being treated. Suitable amounts of dry powders and dry particles to be administered, and dosage schedules for a particular patient can be determined by a clinician of ordinary skill based on these and other considerations.

As used herein, the term "emitted dose" or "ED" refers to an indication of the delivery of a drug formulation from a suitable inhaler device after a firing or dispersion event. More specifically, for dry powder formulations, the ED is a measure of the percentage of powder that is drawn out of a unit dose package and that exits the mouthpiece of an inhaler device. The ED is defined as the ratio of the drug or powder delivered by an inhaler device to the nominal dose (i.e., the mass of drug or powder per unit dose placed into a suitable inhaler device prior to firing). The ED is an experimentally-measured parameter, and can be determined using the method of USP Section 601 Aerosols, Metered-Dose Inhalers and Dry Powder Inhalers, Delivered-Dose Uniformity, Sampling the Delivered Dose from Dry Powder Inhalers, United States Pharmacopeia convention, Rockville, MD, $13^{th}$ Revision, 222-225, 2007. This method utilizes an in vitro device set up to mimic patient dosing. It can also be calculated from the results generated by Next Generation Impactor (NGI) experiments, through summation of all of the drug or powder assayed from the mouthpiece adapter, NGI induction port, and all of the stages within the NGI. The results generated through ED testing per USP 601 and the results generated via the NGI are typically in good agreement.

The term "lung to plasma ratio" or "lung:plasma ratio" refers to the ratio of a concentration of an anti-fungal agent in the lung versus the concentration of the anti-fungal agent in the plasma at either a specific point in time or over a specific range of time. For example, the lung:plasma ratio may be calculated based on concurrent measurements at the maximum concentration (i.e., the "$C_{max}$") of the anti-fungal agent in the lung or in the serum, or at any point in time. The lung:plasma ratio may also be calculated for a total exposure over a certain period of time (i.e., the "area under the curve" or "AUC") such as over a 24 hour period. The lung concentrations of the anti-fungal agent may be assessed by measuring the levels in the sputum, by lung lavage, by biopsy or by some other method. The lung:plasma ratio may be calculated based on concurrent measurements at any point in the dosing cycle and may be calculated based on concurrent measurements before or at steady state.

The term "nominal dose" as used herein refers to an individual dose greater than or equal to 1 mg of anti-fungal agent. The nominal dose is the total dose of anti-fungal agent within one capsule, blister, or ampule.

The terms "FPF (<X)," "FPF (<X microns)," and "fine particle fraction of less than X microns" as used herein, wherein X equals, for example, 3.4 microns, 4.4 microns, 5.0 microns or 5.6 microns, refer to the fraction of a sample of dry particles that have an aerodynamic diameter of less than X microns. For example, FPF (<X) can be determined by dividing the mass of respirable dry particles deposited on stage two and on the final collection filter of a two-stage collapsed Andersen Cascade Impactor (ACI) by the mass of respirable dry particles weighed into a capsule for delivery to the instrument. This parameter may also be identified as "FPF_TD(<X)," where TD means total dose. A similar measurement can be conducted using an eight-stage ACI. An eight-stage ACI cutoffs are different at the standard 60 L/min flowrate, but the FPF_TD(<X) can be extrapolated from the eight-stage complete data set. The eight-stage ACI result can also be calculated by the USP method of using the dose collected in the ACI instead of what was in the capsule to determine FPF. Similarly, a seven-stage next generation impactor (NGI) can be used.

The terms "FPD (<X)", TPD <X microns", FPD(<X microns)" and "fine particle dose of less than X microns" as used herein, wherein X equals, for example, 3.4 microns, 4.4 microns, 5.0 microns or 5.6 microns, refer to the mass of a therapeutic agent delivered by respirable dry particles that have an aerodynamic diameter of less than X micrometers. FPD <X microns can be determined by using an eight-stage Andersen Cascade Impactor (ACI) or a Next Generation Impactor (NGI) at the standard 60 L/min flowrate and summing the mass deposited on the final collection filter, and either directly calculating or extrapolating the FPD value.

The term "respirable" as used herein refers to dry particles or dry powders that are suitable for delivery to the respiratory tract (e.g., pulmonary delivery) in a subject by inhalation. Respirable dry powders or dry particles have a mass median aerodynamic diameter (MMAD) of less than about 10 microns, preferably about 5 microns or less.

As used herein, the term "respiratory tract" includes the upper respiratory tract (e.g., nasal passages, nasal cavity, throat, pharynx, and larynx), respiratory airways (e.g., trachea, bronchi, and bronchioles) and lungs (e.g., respiratory bronchioles, alveolar ducts, alveolar sacs, and alveoli).

As used herein, the term "lower respiratory tract" includes the respiratory airways and lungs.

The term "small" as used herein to describe respirable dry particles refers to particles that have a volume median geometric diameter (VMGD) of about 10 microns or less, preferably about 5 microns or less, or less than 5 microns.

The term "stabilizer" as used herein refers to a compound that improves the physical stability of anti-fungal agents in crystalline particulate form when suspended in a liquid in which the anti-fungal agent is poorly soluble (e.g., reduces the aggregation, agglomeration, Ostwald ripening and/or flocculation of the particulates). Suitable stabilizers are surfactants and amphiphilic materials and include Polysorbates (PS; polyoxyethylated sorbitan fatty acid esters), such as PS20, PS40, PS60 and PS80; fatty acids such as lauric acid, palmitic acid, myristic acid, oleic acid and stearic acid; sorbitan fatty acid esters, such as Span20, Span40, Span60, Span80, and Span 85; phospholipids such as dipalmitoylphosphosphatidylcholine (DPPC), 1,2-Dipalmitoyl-sn-glycero-3-phospho-L-serine (DPPS), 1,2-Dipalmitoyl-sn-glycero-3-phosphocholine (DSPC), 1-palmitoyl-2-oleoylphosphatidylcholine (POPC), and 1,2-Dioleoyl-sn-glycero-3-phosphocholine (DOPC); Phosphatidylglycerols (PGs) such as diphosphatidyl glycerol (DPPG), DSPG, DPPG, POPG, etc.; 1,2-Distearoyl-sn-glycero-3-phosphoethanolamine (DSPE); fatty alcohols; benzyl alcohol, polyoxyethylene-9-lauryl ether; glycocholate; surfactin; poloxomers; polyvinylpyrrolidone (PVP); PEG/PPG block co-polymers (Pluronics/Poloxamers); polyoxyethyene chloresteryl ethers; POE alky ethers; tyloxapol; lecithin; and the like. Preferred stabilizers are polysorbates and fatty acids. A particularly preferred stabilizer is PS80. Another preferred stabilizer is oleic acid.

The term "homogenous dry particle" as used herein refers to particles containing crystalline drug (e.g., nano-crystalline drug) which is pre-processed as a surfactant stabilized suspension. The homogenous dry particle is then formed by spray drying the surfactant-stabilized suspension with (optional) excipients, resulting in dry particles that are compositionally homogenous, or more specifically, identical in their composition of surfactant-coated crystalline drug particles and optionally one or more excipients.

Therapeutic Use and Methods

In one aspect, the invention relates to a method of treating respiratory (e.g., pulmonary) diseases, such as cystic fibrosis, asthma, especially severe asthma, and severely immunocompromised patients, the method comprising administering dry powders and/or respirable dry particles to the respiratory tract of a subject in need thereof, thereby treating respiratory (e.g., pulmonary) diseases, such as cystic fibrosis, asthma, especially severe asthma, and severely immunocompromised patients. This treatment is especially useful in treating *aspergillus* infections (e.g., *Aspergillus fumigatus* infections). This treatment is also useful for treating fungal infections sensitive to itraconazole. Another aspect of the invention is treating allergic bronchopulmonary aspergillosis (ABPA), for example, in patients with pulmonary disease such as asthma or cystic fibrosis. The invention may also allow for treating an individual with a resistant fungal infection by administering an inhaled anti-fungal formulation.

The amount of dry powder administered to the patient may be sufficient to maintain a steady state concentration. As used herein, steady state concentration (Css) refers to the concentration of a drug, in for example lung or plasma, at the time a "steady state" has been achieved, and rates of drug administration and drug elimination are equal. Steady state concentration is a value approached as a limit and is achieved, theoretically, following the last of an infinite number of equal doses given at equal intervals. The maximum value under such conditions (Css,max) is given by Css,max=C0/(1-f), for a drug eliminated by first-order kinetics from a single compartment system. The ratio Css,max/C0 indicates the extent to which drug accumulates under the conditions of a particular dose regimen of, theoretically, an infinitely long duration; the corresponding ratio 1/(1-f) is sometimes called the Accumulation Ratio, R. Css is also the limit achieved, theoretically, at the "end" of an infusion of infinite duration, at a constant rate.

In some aspects, about 2 mg, about 3 mg, about 4 mg, 5 mg, about 10 mg, about 15 mg, about 20 mg, about 25 mg, about 30 mg, about 35 mg, about 40 mg, about 50 mg, about 2 mg to about 35 mg, about 5 mg to about 50 mg, about 10 mg to about 50 mg, about 15 mg to about 50 mg, nominal doses may be administered. The dose and dosing regimen may be selected to achieve a certain lung:plasma ratio, or to achieve certain steady state concentrations in the lung and plasma.

The lung:plasma ratio may be at least about 100:1, at least about 200:1, at least about 300:1, at least about 400:1, at least about 500:1, at least about 600:1, at least about 700:1, at least about 800:1, at least about 1000:1, at least about 1300:1, at least about 1600:1, at least about 1900:1, at least about 2200:1, at least about 2500:1, at least about 2800:1, at least about 3000:1, at least about 3200:1, at least about 3400:1, at least about 3600:1, between 3000:1 to 4000:1, between 3500:1 to 4000:1, or between 3600:1 to 3700:1. Additionally, the lung:plasma ratio may be at least about 2:1, at least 3:1, at least 4:1, at least 5:1, at least 6:1, at least 7:1, at least 8:1, at least 9:1, at least 10:1, at least 15:1, at least 20:1, at least 25:1, at least 50:1, or at least 75:1. The lung:plasma ratio may be calculated based on concurrent measurements at the maximum concentration (i.e., the "$C_{max}$") of the anti-fungal agent in the lung or in the serum, or at any point in time. The lung:plasma ratio may also be calculated for a total exposure over a certain period of time (i.e., the "area under the curve" or "AUC") such as over a 24 hour period. The lung:plasma ratio may be calculated based on concurrent measurements at any point in the dosing cycle and may be calculated before or at steady state.

At steady state, the lung:plasma ratio may be at least about 20:1, at least about 25:1, at least 50:1, at least 75:1, at least about 100:1, at least about 200:1, at least about 300:1, at least about 400:1, at least about 500:1, at least about 600:1, at least about 700:1, at least about 800:1, at least about 1000:1, at least about 1300:1, at least about 1600:1, at least about 1900:1, at least about 2200:1, at least about 2500:1, at least about 2800:1, at least about 3000:1, at least about 3200:1, at least about 3400:1, at least about 3600:1, between 3000:1 to 4000:1, between 3500:1 to 4000:1, or between 3600:1 to 3700:1.

The dry powder formulation may be administered to achieve a plasma concentration. The plasma concentration may be less than 40 ng/mL, less than 35 ng/mL, less than 30 ng/mL, less than 25 ng/mL, less than 20 ng/mL, less than 15 ng/mL, less than 12 ng/mL, less than 10 ng/mL, less than 8 ng/mL, less than 6 ng/mL, less than 4 ng/mL, less than 2 ng/mL, less than 1.5 ng/mL, less than 1.0 ng/mL, less than 0.5 ng/mL, less than 0.3 ng/mL, or less than 0.2 ng/mL.

The dry powder formulation may be administered to achieve a steady state plasma concentration. At steady state, the plasma concentration may be less than 25 ng/mL, less than 20 ng/mL, less than 15 ng/mL, less than 12 ng/mL, less than 10 ng/mL, less than 8 ng/mL, less than 6 ng/mL, less than 4 ng/mL, less than 2 ng/mL, less than 1.5 ng/mL, less than 1.0 ng/mL, less than 0.5 ng/mL, less than 0.3 ng/mL, or less than 0.2 ng/mL. Additionally, the steady state plasma concentration is less than 40 ng/mL, less than 35 ng/mL, or less than 30 ng/mL.

The dry powder formulation may be administered in one or more doses to achieve a lung concentration of about 500 ng/mL, about 800 ng/mL, about 1200 ng/mL, about 1600 ng/mL, about 2000 ng/mL, about 3000 ng/mL, about 4000 ng/mL, about 5000 ng/mL, about 5000 ng/mL, about 6000 ng/mL, about 7000 ng/mL, about 8000 ng/mL, between 2000 ng/mL to 8000 ng/mL, or about 2000 ng/mL to 8100 ng/mL. The lung concentration may be measured at the maximum concentration (i.e., the "$C_{max}$") of the anti-fungal agent in the lung tissue, or at any point in time. The lung concentration may be measured at any point in the dosing cycle and may be calculated before or at steady state.

The dry powder formulation may be administered in one or more doses to achieve a steady state lung concentration of about 500 ng/mL, about 800 ng/mL, about 1200 ng/mL, about 1600 ng/mL, about 2000 ng/mL, about 3000 ng/mL, about 4000 ng/mL, about 5000 ng/mL, about 5000 ng/mL, about 6000 ng/mL, about 7000 ng/mL, about 8000 ng/mL, between 2000 ng/mL to 8000 ng/mL, or about 2000 ng/mL to 8100 ng/mL.

The dry powder formulation may be administered once a day, twice a day, once every other day, or once every three days for approximately 7 days, 14 days, 21 days, 28 days, 1 month, 2 months, 3 months, 4 months, 5 months, 6 months, 1 year, or continuously. In some embodiments, the dry powder formulation is dosed once a day until steady state is achieved, and then less frequently thereafter for up to six months. In some embodiments, one or more fungicidal doses are administered daily until steady state is reached, followed by one or more fungistatic doses (e.g., a lower dose, a less frequently administered dose) for 1 month, 2 months, 3 months, 4 months, 5 months, or 6 months. In some embodiments, one or more doses needed to achieve a fungicidal concentration of anti-fungal agent in the lung is administered daily until steady state is reached, followed by one or more doses (e.g., a lower dose, a less frequently administered dose) needed to achieve a fungistatic concentration of anti-fungal agent in the lung for 1 month, 2 months, 3 months, 4 months, 5 months, or 6 months.

In another aspect of the invention, a fungicidal dose of dry powders and/or respirable dry particles may be administered to the respiratory tract of a subject in need thereof, followed by one or more fungistatic doses of dry powders and/or respirably dry particles, thereby treating respiratory (e.g., pulmonary) diseases, such as cystic fibrosis, asthma, especially severe asthma, and severely immunocompromised patients. The fungistatic dose needed to achieve a minimum inhibitory concentration (MIC) (e.g., MIC50, MIC90) will vary depending on the specific fungus causing the infection, but may be from 0.008-4 μg/mL, from 0.008-0.03 μg/mL, from 0.008-0.06 μg/mL, from 0.03->4 μg/mL, from 0.015-0.5 μg/mL, from 0.004-0.03 μg/mL, from 0.5-1 μg/mL, from 0.5 μg/mL->64 μg/mL, from 0.5-2 μg/mL or from 0.03 mg/L to 32 mg/L. The fungicidal dose needed to achieve a minimum fungicidal concentration (MFC) (e.g., MFC50, MFC90) will vary depending on the specific fungus causing the infection, but may be 0.05 mg/L to greater than 16 mg/L. Various methods and assays for determining lung and plasma concentrations are known in the art and may be used to measure the lung and plasma concentrations during and after administration of the anti-fungal dry powders. For example, bioassays or high performing HPLC may be used to measure the amount of anti-fungal active agent in the lung (e.g., using induced sputum, bronchial lavage, spontaneous sputum) after the patient has been taking the drug for at least 7 days, at least 14 days, at least 21 days, or at least 28 days.

In other aspects, the invention is a method for the treatment, reduction in incidence or severity, or prevention of acute exacerbations caused by a fungal infection in the respiratory tract, such as an *aspergillus* infection. In another aspect, the invention is a method for the treatment, reduction in incidence or severity, or prevention of exacerbations caused by a fungal infection in the respiratory tract, such as an *aspergillus* infection. In another aspect, the invention is a method for the treatment, reduction in incidence or severity, or prevention of exacerbations caused by allergic bronchopulmonary aspergillosis (ABPA), for example, in patients with pulmonary disease such as asthma or cystic fibrosis. In a further aspect, the invention is a method for prophylaxis or treatment of invasive fungal infections in an immunocompromised patient population.

In other aspects, the invention is a method for relieving the symptoms of a respiratory disease and/or a chronic pulmonary disease, such as cystic fibrosis, asthma, especially severe asthma and severely immunocompromised patients. In another aspect, the invention is a method for relieving the symptoms of allergic bronchopulmonary aspergillosis (ABPA) in these patient populations. In yet another aspect, the invention is a method for reducing inflammation, sparing the use of steroids, or reducing the need for steroidal treatment.

In other aspects, the invention is a method for improving lung function of a patient with a respiratory disease and/or a chronic pulmonary disease, such as such as cystic fibrosis, asthma, especially severe asthma and severely immunocompromised patients. In another aspect, the invention is a method for improving lung function of a patient with allergic bronchopulmonary aspergillosis (ABPA).

The dry powders and/or respirable dry particles can be administered to the respiratory tract of a subject in need thereof using any suitable method, such as instillation techniques, and/or an inhalation device, such as a dry powder inhaler (DPI) or metered dose inhaler (MDI). A number of DPIs are available, such as, the inhalers disclosed is U.S. Pat. Nos. 4,995,385 and 4,069,819, Spinhaler® (Fisons, Loughborough, U.K.), Rotahalers®, Diskhaler® and Diskus® (GlaxoSmithKline, Research Triangle Technology Park, N.C.), FlowCaps® (Hovione, Loures, Portugal), Inhalators® (Boehringer-Ingelheim, Germany), Aerolizer® (Novartis, Switzerland), high-resistance, ultrahigh-resistance and low-resistance RS01 (Plastiape, Italy) and others known to those skilled in the art.

The following scientific journal articles are incorporated by reference for their thorough overview of the following dry powder inhaler (DPI) configurations: 1) Single-dose Capsule DPI, 2) Multi-dose Blister DPI, and 3) Multi-dose Reservoir DPI. N. Islam, E. Gladki, "Dry powder inhalers (DPIs)—A review of device reliability and innovation", International Journal of Pharmaceuticals, 360(2008):1-11. H. Chystyn, "Diskus Review", International Journal of Clinical Practice, June 2007, 61, 6, 1022-1036. H. Steckel, B. Muller, "In vitro evaluation of dry powder inhalers I: drug deposition of commonly used devices", International Journal of Pharmaceuticals, 154(1997):19-29. Some representative capsule-based DPI units are RS-01 (Plastiape, Italy), Turbospin® (PH&T, Italy), Brezhaler® (Novartis, Switzerland), Aerolizer (Novartis, Switzerland), Podhaler® (Novartis, Switzerland), HandiHaler® (Boehringer Ingelheim, Germany), AIR® (Civitas, Massachusetts), Dose One® (Dose One, Me.), and Eclipse® (Rhone Poulenc Rorer). Some representative unit dose DPIs are Conix® (3M, Minnesota), Cricket® (Mannkind, California), Dreamboat® (Mannkind, California), Occoris® (Team Consulting, Cambridge, UK), Solis® (Sandoz), Trivair® (Trimel Biopharma, Canada), Twincaps® (Hovione, Loures, Portugal). Some representative blister-based DPI units are Diskus® (GlaxoSmithKline (GSK), UK), Diskhaler® (GSK), Taper Dry® (3M, Minnesota), Gemini® (GSK), Twincer® (University of Groningen, Netherlands), Aspirair® (Vectura, UK), Acu-Breathe® (Respirics, Minnesota, USA), Exubra® (Novartis, Switzerland), Gyrohaler® (Vectura, UK), Omnihaler® (Vectura, UK), Microdose® (Microdose Therapeutix, USA), Multihaler® (Cipla, India) Prohaler® (Aptar), Technohaler® (Vectura, UK), and Xcelovair® (Mylan, Pennsylvania). Some representative reservoir-based DPI units are Clickhaler® (Vectura), Next DPI® (Chiesi), Easyhaler® (Orion), Novolizer® (Meda), Pulmojet® (sanofi-aventis), Pulvinai® (Chiesi), Skyehaler® (Skyepharma), Duohaler® (Vectura), Taifun® (Akela), Flexhaler® (AstraZeneca, Sweden), Turbuhaler® (AstraZeneca, Sweden), and Twisthaler® (Merck), and others known to those skilled in the art.

Generally, inhalation devices (e.g., DPIs) are able to deliver a maximum amount of dry powder or dry particles in a single inhalation, which is related to the capacity of the blisters, capsules (e.g., size 000, 00, 0E, 0, 1, 2, 3 and 4, with respective volumetric capacities of 1.37 ml, 950 μl, 770 μl, 680 μl, 480 μl, 360 μl, 270 μl and 200 μl) or other means that contain the dry powders and/or respirable dry particles within the inhaler. Preferably, the blister has a volume of about 360 microliters or less, about 270 microliters or less, or more preferably, about 200 microliters or less, about 150 microliters or less, or about 100 microliters or less. Preferably, the capsule is a size 2 capsule, or a size 4 capsule. More preferably, the capsule is a size 3 capsule. Accordingly, delivery of a desired dose or effective amount may require two or more inhalations. Preferably, each dose that is administered to a subject in need thereof contains an effective amount of respirable dry particles or dry powder and is administered using no more than about 4 inhalations. For example, each dose of dry powder or respirable dry particles can be administered in a single inhalation or 2, 3, or 4 inhalations. The dry powders and/or respirable dry particles are preferably administered in a single, breath-activated step using a passive DPI. When this type of device is used, the energy of the subject's inhalation both disperses the respirable dry particles and draws them into the respiratory tract.

Dry powders and/or respirable dry particles suitable for use in the methods of the invention can travel through the upper airways (i.e., the oropharynx and larynx), the lower airways, which include the trachea followed by bifurcations into the bronchi and bronchioli, and through the terminal bronchioli which in turn divide into respiratory bronchioli leading then to the ultimate respiratory zone, the alveoli or the deep lung. In one embodiment of the invention, most of the mass of respirable dry particles deposit in the deep lung. In another embodiment of the invention, delivery is primarily to the central airways. In another embodiment, delivery is to the upper airways. In a preferred embodiment, most of the mass of the respirable dry particles deposit in the conducting airways.

If desired or indicated, the dry powders and respirable dry particles described herein can be administered with one or more other therapeutic agents. The other therapeutic agents can be administered by any suitable route, such as orally, parenterally (e.g., intravenous, intra-arterial, intramuscular, or subcutaneous injection), topically, by inhalation (e.g., intrabronchial, intranasal or oral inhalation, intranasal drops), rectally, vaginally, and the like. The respirable dry particles and dry powders can be administered before, substantially concurrently with, or subsequent to administration of the other therapeutic agent. Preferably, the dry powders and/or respirable dry particles and the other therapeutic agent are administered so as to provide substantial overlap of their pharmacologic activities.

The dry powders and respirable dry particles described herein are intended to be inhaled as such, and the present invention excludes the use of the dry powder formulation in making an extemporaneous dispersion. An extemporaneous dispersion is known by those skilled in the art as a preparation completed just before use, which means right before the administration of the drug to the patient. As used herein, the term "extemporaneous dispersion" refers to all of the cases in which the solution or suspension is not directly produced by the pharmaceutical industry and commercialized in a ready to be used form, but is prepared in a moment that follows the preparation of the dry solid composition, usually in a moment close to the administration to the patient.

Dry Powders and Dry Particles

The dry powder formulations may comprise respirable dry particles that contain 1) an anti-fungal agent in crystalline particulate form, 2) a stabilizer, and 3) one or more excipients. Any desired anti-fungal agents can be included in the formulations described herein. Many anti-fungal agents are well-known, for example, polyene anti-fungals, such as amphotericin B; triazole anti-fungals, such as itraconazole, ketoconazole, fluconazole, voriconazole, and posaconazole; echinocandin anti-fungals, such as caspofungin, micafungin, and an idulafungin. Other triazole anti-fungals include clotrimazole, Isavuconazole, and miconazole. Included are a new chemical class of triterpenoid glucan synthase inhibitors, for example, SCY-078. Also included are orotomide anti-fungals, such as F901318, which inhibits dihydroorotate dehydrogenase. Other anti-fungal agents include: acoziborole, amorolfine, amorolfine hydrochloride, arasertaconazole nitrate, bifonazole, butenafine hydrochloride, butoconazole nitrate, carvacrol, chloramine-T, ciclopirox, ciclopirox, ciclopirox olamine, croconazole hydrochloride, eberconazole, econazole, econazole nitrate, Fenarimol, fenticonazole nitrate, flucytosine, flucytosine, flutrimazole, formaldehyde, fosravuconazole, griseofulvin, isavuconazonium sulphate, isoconazole nitrate, lanoconazole, liranaftate, luliconazole, miconazole nitrate, naftifine, natamycin, nikkomycin Z, Novexatin, nystatin, oteseconazole, oxiconazole nitrate, piroctone olamine, quilseconazole, rezafungin acetate, SCY-078 citrate, selenium sulfide, sertaconazole nitrate, sulconazole nitrate, taurolidine, tavaborole, terbinafine, terbinafine hydrochloride, terconazole, thiabendazole, tioconazole, tolnaftate, undecylenic acid, and zinc pyrithione.

The crystallinity of the anti-fungal agent, as well as the size of the anti-fungal subparticles, appears to be important for effective therapy and for reduced toxicity in the lung. Without wishing to be bound by any particular theory, it is believed that smaller subparticles of anti-fungal agent in crystalline form will dissolve in the airway lining fluid more rapidly than larger particles—in part due to the larger amount of surface area. It is also believed that crystalline anti-fungal agent will dissolve more slowly in the airway lining fluid than amorphous anti-fungal agent. Accordingly, the dry powders described herein can be formulated using anti-fungal agents in crystalline particulate form that provide for a desired degree of crystallinity and sub-particle size, and can be tailored to achieve desired pharmacokinetic properties while avoiding unacceptable toxicity in the lungs.

The respirable dry particles contain about 1% to about 95% anti-fungal agent by weight (wt %). It is preferred that the respirable dry particle contains an amount of anti-fungal agent so that a therapeutically effective dose can be administered and maintained without the need to inhale large volumes of dry powder more than three time a day. For example, it is preferred that the respirable dry particles contain about 1% to 95%, about 10% to 75%, about 15% to 75%, about 25% to 75%, about 30% to 70%, about 40% to 60%, about 50% to about 90%, about 50% to about 70%, about 70% to about 90%, about 60% to about 80%, about 20%, about 50%, about 70%, or about 80% anti-fungal agent by weight (wt %). The respirable dry particles may contain about 75%, about 80%, about 85%, about 90%, or about 95% anti-fungal agent by weight (wt %). In particular embodiments, the range of anti-fungal agent in the respirable dry particles is about 40% to about 90%, about 55% to about 85%, about 55% to about 75%, or about 65% to about 85%, by weight (wt %). The amount of anti-fungal agent present in the respirable dry particles by weight is also referred to as the "drug load."

The anti-fungal agent is present in the respirable dry particles in crystalline particulate form (e.g., nano-crystalline). More specifically, in the form of a sub-particle that is about 50 nm to about 5,000 nm (Dv50), preferably, with the anti-fungal agent being at least 50% crystalline. For example, for any desired drug load, the sub-particle size can be about 100 nm, about 300 nm, about 1500 nm, about 80 nm to about 300 nm, about 80 nm to about 250 nm, about 80 nm to about 200 nm, about 100 nm to about 150 nm, about 1200 nm to about 1500 nm, about 1500 nm to about 1750 nm, about 1200 nm to about 1400 nm, or about 1200 nm to about 1350 nm (Dv50). In particular embodiments, the sub-particle is between about 50 nm to about 2500 nm, between about 50 nm and 1000 nm, between about 50 nm and 800 nm, between about 50 nm and 600 nm, between about 50 nm and 500 nm, between about 50 nm and 400 nm, between about 50 nm and 300 nm, between about 50 nm and 200 nm, or between about 100 nm and 300 nm. In addition, for any desired drug load and sub-particle size, the degree of anti-fungal agent crystallinity can be at least about 50%, at least about 60%, at least about 70%, at least about 80%, at least about 90%, at least about 95%, or about 100% crystalline. Preferably, the anti-fungal agent is about 100% crystalline.

The anti-fungal agent in crystalline particulate form can be prepared in any desired sub-particle size using a suitable method, including a stabilizer if desired, such as by wet milling, jet milling or other suitable method.

The respirable dry particles also include a stabilizer. The stabilizer helps maintain the desired size of the anti-fungal agent in crystalline particulate form during wet milling, in spray drying feedstock, and aids in wetting and dispersing. It is preferred to use as little stabilizer as is needed to obtain the desired dry powder. The amount of stabilizer is typically related to the amount of anti-fungal agent present in the dry particle and can range from about 1:1 (anti-fungal agent: stabilizer (wt:wt)) to about 50:1 (wt:wt), with ≥ (greater than or equal to) 10:1 being preferred. For example, the ratio of anti-fungal agent:stabilizer (wt:wt) in the dry particles can be ≥ (greater than or equal to) 10:1, about 10:1, about 20:1, about 1:1 to about 50:1, about 10:1 to about 15:1, or about 10:1 to about 20:1. In particular embodiments, the ratio is about 5:1 to about 20:1, about 7:1 to about 15:1, or about 9:1 to about 11:1. In addition, the amount of stabilizer that is present in the dry particles can be in a range of about 0.05% to about 45% by weight (wt %). In particular embodiments, the range is about 1% to about 15%, about 4% to about 10%, or about 5% to about 8% by weight (wt %). It is generally preferred that the respirable dry particles contain less than about 10% stabilizer by weight (wt %), such as 9 wt % or less, 8 wt % or less, 7 wt % or less, 5 wt % or less, or about 1 wt %. Alternatively, the respirable dry particles contain about 5 wt %, about 6 wt %, about 7 wt %, about 7.5 wt %, about 8 wt %, or about 10% stabilizer. A particularly preferred stabilizer for use in the dry powders described herein is polysorbate 80. Another preferred stabilizer is oleic acid (or salt forms thereof). In contrast to the prior art, which uses surfactant to prevent the onset of crystallization in the produced dry powder, the surfactant in the present invention is added to stabilize a colloidal suspension of the crystalline drug in an anti-solvent.

The respirable dry particles also include any suitable and desired amount of one or more excipients. The dry particles can contain a total excipient content of about 10 wt % to about 99 wt %, with about 25 wt % to about 85 wt %, or about 40 wt % to about 55 wt % being more typical. The dry particles can contain a total excipient content of about 1 wt %, about 2 wt %, about 4 wt %, about 6 wt %, about 8 wt %, or less than about 10 wt %. In particular embodiments, the range is about 5% to about 50%, about 15% to about 50%, about 25% to about 50%, about 5% to about 40%, about 5% to about 30%, about 5% to about 20%, or about 5% to about 15%. In other embodiments, the range of excipient is about 1% to about 9%, about 2% to about 9%, about 3% to about 9%, about 4% to about 9%, about 5% to about 9%, about 1% to about 8%, about 2% to about 8%, about 3% to about 8%, about 4% to about 8%, about 5% to about 8%, about 1% to about 7%, about 2% to about 7%, about 3% to about 7%, about 4% to about 7%, about 5% to about 7%, about 1% to about 6%, about 2% to about 6%, about 3% to about 6%, or about 1% to about 5%.

Many excipients are well-known in the art and can be included in the dry powders and dry particles described herein. Pharmaceutically acceptable excipients that are particularly preferred for the dry powders and dry particles described herein include monovalent and divalent metal cation salts, carbohydrates, sugar alcohols and amino acids.

Suitable monovalent metal cation salts, include, for example, sodium salts and potassium salts. Suitable sodium salts that can be present in the respirable dry particles of the invention include, for example, sodium chloride, sodium citrate, sodium sulfate, sodium lactate, sodium acetate, sodium bicarbonate, sodium carbonate, sodium stearate, sodium ascorbate, sodium benzoate, sodium biphosphate, sodium phosphate, sodium bisulfite, sodium borate, sodium gluconate, sodium metasilicate and the like.

Suitable potassium salts include, for example, potassium chloride, potassium bromide, potassium iodide, potassium bicarbonate, potassium nitrite, potassium persulfate, potassium sulfite, potassium bisulfite, potassium phosphate, potassium acetate, potassium citrate, potassium glutamate, dipotassium guanylate, potassium gluconate, potassium malate, potassium ascorbate, potassium sorbate, potassium succinate, potassium sodium tartrate and any combination thereof.

Suitable divalent metal cation salts, include magnesium salts and calcium salts. Suitable magnesium salts include, for example, magnesium lactate, magnesium fluoride, magnesium chloride, magnesium bromide, magnesium iodide, magnesium phosphate, magnesium sulfate, magnesium sulfite, magnesium carbonate, magnesium oxide, magnesium nitrate, magnesium borate, magnesium acetate, magnesium citrate, magnesium gluconate, magnesium maleate, magnesium succinate, magnesium malate, magnesium taurate, magnesium orotate, magnesium glycinate, magnesium naphthenate, magnesium acetylacetonate, magnesium formate, magnesium hydroxide, magnesium stearate, magnesium hexafluorsilicate, magnesium salicylate or any combination thereof.

Suitable calcium salts include, for example, calcium chloride, calcium sulfate, calcium lactate, calcium citrate, calcium carbonate, calcium acetate, calcium phosphate, calcium alginate, calcium stearate, calcium sorbate, calcium gluconate and the like.

A preferred sodium salt is sodium sulfate. A preferred sodium salt is sodium chloride. A preferred sodium salt is sodium citrate. A preferred magnesium salt is magnesium lactate.

Carbohydrate excipients that are useful in this regard include the mono- and polysaccharides. Representative monosaccharides include dextrose (anhydrous and the monohydrate; also referred to as glucose and glucose monohydrate), galactose, D-mannose, sorbose and the like. Representative disaccharides include lactose, maltose, sucrose, trehalose and the like. Representative trisaccharides include raffinose and the like. Other carbohydrate excipients including dextran, maltodextrin and cyclodextrins, such as 2-hydroxypropyl-beta-cyclodextrin can be used as desired. Representative sugar alcohols include mannitol, sorbitol and the like. A preferred sugar alcohol is mannitol. Preferred carbohydrates are mannitol, lactose, maltodextrin and trehalose.

Suitable amino acid excipients include any of the naturally occurring amino acids that form a powder under standard pharmaceutical processing techniques and include the non-polar (hydrophobic) amino acids and polar (uncharged, positively charged and negatively charged) amino acids, such amino acids are of pharmaceutical grade and are generally regarded as safe (GRAS) by the U.S. Food and Drug Administration. Representative examples of non-polar amino acids include alanine, isoleucine, leucine, methionine, phenylalanine, proline, tryptophan and valine. Representative examples of polar, uncharged amino acids include cysteine, glycine, glutamine, serine, threonine, and tyrosine. Representative examples of polar, positively charged amino acids include arginine, histidine and lysine. Representative examples of negatively charged amino acids include aspartic acid and glutamic acid. A preferred amino acid is leucine.

In one aspect, the respirable dry particles comprise leucine as one of the one or more excipients in an amount of about 1% to about 9%, about 2% to about 9%, about 3% to about 9%, about 4% to about 9%, about 5% to about 9%, about 1% to about 8%, about 2% to about 8%, about 3% to about 8%, about 4% to about 8%, about 5% to about 8%, about 1% to about 7%, about 2% to about 7%, about 3% to about 7%, about 4% to about 7%, about 5% to about 7%, about 1% to about 6%, about 2% to about 6%, about 3% to about 6%, about 1% to about 5%, about 1%, about 2%, about 3%, about 4%, about 5%, about 6%, about 7%, about 9%, or about 10%. On another aspect, the respirable dry particles comprise leucine as one of the one or more excipients in an amount of 10% or greater.

The dry particles described herein contain 1) an anti-fungal agent in crystalline particulate form, 2) a stabilizer, and optionally 3) one or more excipients. In some aspects, the dry particles contain a first excipient that is a monovalent or divalent metal cation salt, and a second excipient that is an amino acid, carbohydrate or sugar alcohol. For example, the first excipient can be a sodium salt or a magnesium salt, and the second excipient can be an amino acid (such as leucine). In more particular examples, the first excipient can be sodium sulfate, sodium chloride or magnesium lactate, and the second excipient can be leucine. Even more particularly, the first excipient can be sodium sulfate and the second excipient can be leucine. In another example, the first excipient can be a sodium salt or a magnesium salt, and the second excipient can be a sugar alcohol (such as mannitol). In more particular examples, the first excipient can be sodium sulfate, sodium chloride or magnesium lactate, and the second excipient can be mannitol. In another example, the first excipient can be a sodium salt or a magnesium salt, and the second excipient can be a carbohydrate (such as maltodextrin). In other examples, the dry particles include an anti-fungal agent in crystalline particulate form, a stabilizer and one excipient, for example a sodium salt, a magnesium salt or an amino acid (e.g. leucine).

In one aspect, the dry powder formulations comprise respirable dry particles comprising 1) an anti-fungal agent in crystalline particulate form, 2) a stabilizer, and 3) one or more excipients, with the proviso that the anti-fungal agent is not a polyene anti-fungal (e.g., amphotericin B).

In one preferred aspect, the dry powder formulations comprise respirable dry particles comprising 1) a triazole anti-fungal agent in crystalline particulate form, 2) a stabilizer, and 3) one or more excipients.

In one aspect, the dry powder formulations comprise respirable dry particles comprising: (i) about 50% to about 80% of a triazole anti-fungal agent in crystalline particulate form, about 4% to about 40% of a stabilizer, and about 1% to about 9% of one or more excipients; (ii) about 45% to about 85% of a triazole anti-fungal agent in crystalline particulate form, about 3% to about 15% of a stabilizer, about 3% to about 50% sodium salt, and about 1% to 9% of one or more amino acids; (iii) about 45% to about 85% of a triazole anti-fungal agent in crystalline particulate form, about 3% to about 15% of a stabilizer, about 3% to about 50% sodium sulfate, and about 1% to 9% of leucine; (iv) about 45% to about 85% of a triazole anti-fungal agent in crystalline particulate form, about 3% to about 15% of a stabilizer, about 3% to about 50% sodium salt, and about 1% to about 8% of one or more amino acids; or (v) about 45% to about 85% of a triazole anti-fungal agent in crystalline particulate form, about 3% to about 15% of a stabilizer, about 3% to about 50% sodium sulfate, and about 1% to about 8% leucine; where all percentages are weight percentages, and all formulations add up to 100% on a dry basis.

In a particularly preferred aspect, the dry powder formulations comprise respirable dry particles comprising 1) itraconazole in crystalline particulate form, 2) a stabilizer, and 3) one or more excipients. In this particularly preferred aspect, the dry powder formulation does not comprise lactose. Specific formulations of this particularly preferred embodiment are below. In Table 1 below, these examples are further specified for itraconazole in crystalline particulate form at specific itraconazole crystalline sizes, also referred to as itraconazole subparticles.

In one aspect, the dry powder formulation comprises 50% Itraconazole, 35% sodium sulfate, 10% leucine, and 5% polysorbate 80.

In one aspect, the dry powder formulation comprises 50% Itraconazole, 37% sodium sulfate, 8% leucine, and 5% polysorbate 80.

In another aspect, the dry powder formulation comprises 60% Itraconazole, 26% sodium sulfate, 8% leucine, and 6% polysorbate 80.

In another aspect, the dry powder formulation comprises 70% Itraconazole, 15% sodium, 8% leucine, and 7% polysorbate 80.

In another aspect, the dry powder formulation comprises 75% Itraconazole, 9.5% sodium sulfate, 8% leucine, and 7.5% polysorbate 80.

In another aspect, the dry powder formulation comprises 80% Itraconazole, 4% sodium sulfate, 8% leucine, and 8% polysorbate 80.

In another aspect, the dry powder formulation comprises 80% Itraconazole, 10% sodium sulfate, 2% leucine, and 8% polysorbate 80.

In another aspect, the dry powder formulation comprises 80% Itraconazole, 11% sodium sulfate, 1% leucine, and 8% polysorbate 80.

In one aspect, the dry powder formulation comprises 50% Itraconazole, 35% sodium chloride, 10% leucine, and 5% polysorbate 80.

In one aspect, the dry powder formulation comprises 50% Itraconazole, 37% sodium chloride, 8% leucine, and 5% polysorbate 80.

In another aspect, the dry powder formulation comprises 60% Itraconazole, 26% sodium chloride, 8% leucine, and 6% polysorbate 80.

In another aspect, the dry powder formulation comprises 70% Itraconazole, 15% sodium chloride, 8% leucine, and 7% polysorbate 80.

In another aspect, the dry powder formulation comprises 75% Itraconazole, 9.5% sodium chloride, 8% leucine, and 7.5% polysorbate 80.

In another aspect, the dry powder formulation comprises 80% Itraconazole, 4% sodium chloride, 8% leucine, and 8% polysorbate 80.

In another aspect, the dry powder formulation comprises 80% Itraconazole, 10% sodium chloride, 2% leucine, and 8% polysorbate 80.

In another aspect, the dry powder formulation comprises 80% Itraconazole, 11% sodium chloride, 1% leucine, and 8% polysorbate 80.

The dry powders and/or respirable dry particles are preferably small, mass dense, and dispersible. To measure volumetric median geometric diameter (VMGD), a laser diffraction system may be used, e.g., a Spraytec system (particle size analysis instrument, Malvern Instruments) and a HELOS/RODOS system (laser diffraction sensor with dry dispensing unit, Sympatec GmbH). The respirable dry particles have a VMGD as measured by laser diffraction at the dispersion pressure setting (also called regulator pressure) of 1.0 bar at a maximum orifice ring pressure using a HELOS/RODOS system of about 10 microns or less, about 5 microns or less, about 4 μm or less, about 3 μm or less, about 1 μm to about 5 μm, about 1 μm to about 4 about 1.5 μm to about 3.5 μm, about 2 μm to about 5 μm, about 2 μm to about 4 μm, or about 2 μm to about 3 μm. Preferably, the VMGD is about 5 microns or less or about 4 μm or less. In one aspect, the dry powders and/or respirable dry particles have a minimum VMGD of about 0.5 microns or about 1.0 micron.

The dry powders and/or respirable dry particles preferably have 1 bar/4 bar dispersibility ratio and/or 0.5 bar/4 bar dispersibility ratio of less than about 2.0 (e.g., about 0.9 to less than about 2), about 1.7 or less (e.g., about 0.9 to about 1.7) about 1.5 or less (e.g., about 0.9 to about 1.5), about 1.4 or less (e.g., about 0.9 to about 1.4), or about 1.3 or less (e.g., about 0.9 to about 1.3), and preferably have a 1 bar/4 bar and/or a 0.5 bar/4 bar of about 1.5 or less (e.g., about 1.0 to about 1.5), and/or about 1.4 or less (e.g., about 1.0 to about 1.4).

The dry powders and/or respirable dry particles preferably have a tap density of at least about 0.2 $g/cm^3$, of at least about 0.25 $g/cm^3$, a tap density of at least about 0.3 $g/cm^3$, of at least about 0.35 $g/cm^3$, a tap density of at least 0.4 $g/cm^3$. For example, the dry powders and/or respirable dry particles have a tap density of greater than 0.4 $g/cm^3$ (e.g., greater than 0.4 $g/cm^3$ to about 1.2 $g/cm^3$), a tap density of at least about 0.45 $g/cm^3$ (e.g., about 0.45 $g/cm^3$ to about 1.2 $g/cm^3$), at least about 0.5 $g/cm^3$ (e.g., about 0.5 $g/cm^3$ to about 1.2 $g/cm^3$), at least about 0.55 $g/cm^3$ (e.g., about 0.55 $g/cm^3$ to about 1.2 $g/cm^3$), at least about 0.6 $g/cm^3$ (e.g., about 0.6 $g/cm^3$ to about 1.2 $g/cm^3$) or at least about 0.6 $g/cm^3$ to about 1.0 $g/cm^3$. Alternatively, the dry powders and/or respirable dry particles preferably have a tap density of about 0.01 $g/cm^3$ to about 0.5 $g/cm^3$, about 0.05 $g/cm^3$ to about 0.5 $g/cm^3$, about 0.1 $g/cm^3$ to about 0.5 $g/cm^3$, about 0.1 $g/cm^3$ to about 0.4 $g/cm^3$, or about 0.1 $g/cm^3$ to about 0.4 $g/cm^3$. Alternatively, the dry powders and/or respirable dry particles have a tap density of about 0.15 $g/cm^3$ to about 1.0 $g/cm^3$. Alternatively, the dry powders and/or respirable dry particles have a tap density of about 0.2 $g/cm^3$ to about 0.8 $g/cm^3$.

The dry powders and/or respirable dry particles have a bulk density of at least about 0.1 $g/cm^3$, or at least about 0.8 $g/cm^3$. For example, the dry powders and/or respirable dry particles have a bulk density of about 0.1 $g/cm^3$ to about 0.6 $g/cm^3$, about 0.2 $g/cm^3$ to about 0.7 $g/cm^3$, about 0.3 $g/cm^3$ to about 0.8 $g/cm^3$.

The respirable dry particles, and the dry powders when the dry powders are respirable dry powders, preferably have an MMAD of less than 10 microns, preferably an MMAD of about 5 microns or less, or about 4 microns or less. In one aspect, the respirable dry powders and/or respirable dry particles preferably have a minimum MMAD of about 0.5 microns, or about 1.0 micron. In one aspect, the respirable dry powders and/or respirable dry particles preferably have a minimum MMAD of about 2.0 microns, about 3.0 microns, or about 4.0 microns.

The dry powders and/or respirable dry particles preferably have a FPF of less than about 5.6 microns (FPF<5.6 μm) of the total dose of at least about 35%, preferably at least about 45%, at least about 60%, between about 45% to about 80%, or between about 60% and about 80%.

The dry powders and/or respirable dry particles preferably have a FPF of less than about 3.4 microns (FPF<3.4 μm) of the total dose of at least about 20%, preferably at least about 25%, at least about 30%, at least about 40%, between about 25% and about 60%, or between about 40% and about 60%.

The dry powders and/or respirable dry particles preferably have a total water and/or solvent content of up to about 15% by weight, up to about 10% by weight, up to about 5% by weight, up to about 1%, or between about 0.01% and about 1%, or may be substantially free of water or other solvent.

The dry powders and/or respirable dry particles preferably may be administered with low inhalation energy. In order to relate the dispersion of powder at different inhalation flow rates, volumes, and from inhalers of different resistances, the energy required to perform the inhalation maneuver may be calculated. Inhalation energy can be calculated from the equation $E=R^2Q^2V$ where E is the inhalation energy in Joules, R is the inhaler resistance in $kPa^{1/2}/LPM$, Q is the steady flow rate in L/min and V is the inhaled air volume in L.

Healthy adult populations are predicted to be able to achieve inhalation energies ranging from 2.9 Joules for comfortable inhalations to 22 Joules for maximum inhalations by using values of peak inspiratory flow rate (PIFR) measured by Clarke et al. (Journal of Aerosol Med, 6(2), p. 99-110, 1993) for the flow rate Q from two inhaler resistances of 0.02 and 0.055 $kPa^{112}/LPM$, with an inhalation volume of 2L based on both FDA guidance documents for dry powder inhalers and on the work of Tiddens et al. (Journal of Aerosol Med, 19(4), p. 456-465, 2006) who found adults averaging 2.2L inhaled volume through a variety of DPIs.

Mild, moderate and severe adult COPD patients are predicted to be able to achieve maximum inhalation energies of 5.1 to 21 Joules, 5.2 to 19 Joules, and 2.3 to 18 Joules respectively. This is again based on using measured PIFR values for the flow rate Q in the equation for inhalation energy. The PIFR achievable for each group is a function of the inhaler resistance that is being inhaled through. The work of Broeders et al. (Eur Respir J, 18, p. 780-783, 2001) was used to predict maximum and minimum achievable PIFR through two dry powder inhalers of resistances 0.021 and 0.032 $kPa^{1/2}/LPM$ for each.

Similarly, adult asthmatic patients are predicted to be able to achieve maximum inhalation energies of 7.4 to 21 Joules based on the same assumptions as the COPD population and PIFR data from Broeders et al.

Healthy adults and children, COPD patients, asthmatic patients ages 5 and above, and CF patients, for example, are capable of providing sufficient inhalation energy to empty and disperse the dry powder formulations of the invention.

The dry powders and/or respirable dry particles are preferably characterized by a high emitted dose, such as a CEPM of at least 75%, at least 80%, at least 85%, at least 90%, at least 95%, from a passive dry powder inhaler subject to a total inhalation energy of about 5 Joules, about 3.5 Joules, about 2.4 Joules, about 2 Joules, about 1 Joule, about 0.8 Joules, about 0.5 Joules, or about 0.3 Joules is applied to the dry powder inhaler. The receptacle holding the dry powders and/or respirable dry particles may contain about 5 mg, about 7.5 mg, about 10 mg, about 15 mg, about 20 mg, or about 30 mg. In one aspect, the dry powders and/or respirable dry particles are characterized by a CEPM of 80% or greater and a VMGD of 5 microns or less when emitted from a passive dry powder inhaler having a resistance of about 0.036 sqrt(kPa)/liters per minute under the following conditions: an air flow rate of 30 LPM, run for 3 seconds using a size 3 capsule that contains a total mass of 10 mg. In another aspect, the dry powders and/or respirable dry particles are characterized by a CEPM of 80% or greater and a VMGD of 5 microns or less when emitted from a passive dry powder inhaler having a resistance of about 0.036 sqrt(kPa)/liters per minute under the following conditions: an air flow rate of 20 LPM, run for 3 seconds using a size 3 capsule that contains a total mass of 10 mg. In a further aspect, the dry powders and/or respirable dry particles are characterized by a CEPM of 80% or greater and a VMGD of 5 microns or less when emitted from a passive dry powder inhaler having a resistance of about 0.036 sqrt(kPa)/liters per minute under the following conditions: an air flow rate of 15 LPM, run for 4 seconds using a size 3 capsule that contains a total mass of 10 mg.

The dry powder can fill the unit dose container, or the unit dose container can be at least 2% full, at least 5% full, at least 10% full, at least 20% full, at least 30% full, at least 40% full, at least 50% full, at least 60% full, at least 70% full, at least 80% full, or at least 90% full. The unit dose container can be a capsule (e.g., size 000, 00, 0E, 0, 1, 2, 3, and 4, with respective volumetric capacities of 1.37 ml, 950 μl, 770 μl, 680 μl, 480 μl, 360 μl, 270 μl, and 200 μl). The capsule can be at least about 2% full, at least about 5% full, at least about 10% full, at least about 20% full, at least about 30% full, at least about 40% full, or at least about 50% full. The unit dose container can be a blister. The blister can be packaged as a single blister or as part of a set of blisters, for example, 7 blisters, 14 blisters, 28 blisters or 30 blisters. The one or more blister can be preferably at least 30% full, at least 50% full or at least 70% full.

An advantage of the powders is that they disperse well across a wide range of flow rates and are relatively flowrate independent. The dry powders and/or respirable dry particles enable the use of a simple, passive DPI for a wide patient population.

In particular aspects, the dry powders and/or respirable dry particles that comprise anti-fungal agent in crystalline particulate form, also referred to as anti-fungal subparticles, (e.g., anti-fungal subparticle size of about 80 nm to about 1750 nm, such as about 60 nm to about 175 nm, about 150 nm to about 400 nm or about 1200 nm to about 1750 nm), a stabilizer, and optionally one or more excipients. Particular dry powders and respirable dry particles have the following formulations shown in Table 1. The dry powders and/or respirable dry particles described herein are preferably characterized by: 1) a VMGD at 1 bar as measured using a HELOS/RODOS system of about 10 microns or less, preferably about 5 microns or less; 2) a 1 bar/4 bar dispersibility ratio and/or a 0.5 bar/4 bar dispersibility ratio of about 1.5 or less, about 1.4 or less or about 1.3 or less; 3) a MMAD of about 10 microns or less, preferably about 5 microns or less; 4) a FPF<5.6 μm of the total dose of at least about 45% or at least about 60%; and/or 5) a FPF<3.4 μm of the total dose of at least about 25% or at least about 40%. If desired, the dry powders and/or respirable dry particles are further characterized by a tap density of about 0.2 g/cm$^3$ or greater, about 0.3 g/cm$^3$ or greater, about 0.4 g/cm$^3$ or greater, greater than 0.4 g/cm$^3$, about 0.45 g/cm$^3$ or greater or about 0.5 g/cm$^3$ or greater.

TABLE 1

| Formulation | Anti-fungal (wt %) | Excipients (wt %) | Stabilizer (wt %) | Anti-fungal subparticle size (left column), and range (right column) (Dv50 nm) | |
|---|---|---|---|---|---|
| A (I) | Itraconazole 20% | Sodium sulfate 39%<br>Mannitol 39% | PS80 2% | 124 | 60-175 |
| B (II) | Itraconazole 50% | Sodium sulfate 22.5%<br>Mannitol 22.5% | PS80 5% | 124 | 60-175 |
| C (III) | Itraconazole 20% | Sodium chloride 62.4%<br>Leucine 15.6% | PS80 2% | 124 | 60-175 |
| D (IV) | Itraconazole 50% | Sodium chloride 36%<br>Leucine 9% | PS80 5% | 124 | 60-175 |
| E (V) | Itraconazole 20% | Magnesium lactate 66.3%<br>Leucine 11.7% | PS80 2% | 124 | 60-175 |
| F (VI) | Itraconazole 50% | Magnesium lactate 38.25%<br>Leucine 6.75% | PS80 5% | 124 | 60-175 |
| G (VII) | Itraconazole 50% | Sodium sulfate 33.25%<br>Leucine 14.25% | Oleic acid 2.5% | 120 | 60-175 |
| H (VIII) | Itraconazole 70% | Sodium sulfate 13.25%<br>Leucine 13.25% | Oleic acid 3.5% | 120 | 60-175 |
| I | Itraconazole 50% | Magnesium lactate 33.25%<br>Leucine 14.25% | Oleic acid 2.5% | 120 | 60-175 |
| J | Itraconazole 70% | Magnesium lactate 13.25%<br>Leucine 13.25% | Oleic acid 3.5% | 120 | 60-175 |
| K (XI) | Itraconazole 50% | Sodium sulfate 35%<br>Leucine 12.5% | Oleic acid 2.5% | 126 | 60-175 |
| L (XII) | Itraconazole 50% | Sodium sulfate 35%<br>Leucine 10% | PS80 5% | 132 | 60-175 |
| M (XIII) | Itraconazole 50% | Sodium sulfate 35%<br>Leucine 10% | PS80 5% | 198 | 150-250 |
| N (XIV) | Itraconazole 50% | Sodium sulfate 35%<br>Leucine 10% | PS80 5% | 258 | 200-325 |
| O (XV) | Itraconazole 50% | Sodium sulfate 35%<br>Leucine 10% | PS80 5% | 1600 | 1200-1650 |
| P (XVI) | Itraconazole 50% | Sodium sulfate 35%<br>Leucine 10% | PS80 <5% | 1510 | 1200-1650 |

TABLE 1-continued

| Formulation | Anti-fungal (wt %) | Excipients (wt %) | Stabilizer (wt %) | Anti-fungal subparticle size (left column), and range | (right column) (Dv50 nm) |
|---|---|---|---|---|---|
| Q (XVII) | Amphotericin B 50% | Sodium sulfate 35% Leucine 10% | PS80 5% | 120 | 60-175 |
| R (XVIII) | Amphotericin B 50% | Sodium chloride 35% Leucine 10% | PS80 5% | 120 | 60-175 |
| S (XIX) | Itraconazole 50% | Sodium sulfate 35% Leucine 15% | N/A | N/A | N/A Itraconazole in amorphous form |
| XX | Itraconazole 50% | Sodium sulfate 35% Leucine 15% | N/A | N/A | N/A Itraconazole in amorphous form |
| XXI | Itraconazole 50% | Sodium sulfate 35%, Leucine 10% | PS80 5% | 130 | 60-175 |
| XXII | Itraconazole 50% | Sodium sulfate 35%, Leucine 11.57% | Oleic acid 3.43% | 115 | 60-175 |
| XXIII | Itraconazole 50% | Sodium sulfate 35%, Leucine 13.75% | PS80 1.25% | 1640 | 1200-1650 |
| XXIV | Itraconazole 50% | Sodium sulfate 37%, Leucine 8% | PS80 5% | 130 | 60-175 |
| XXV | Itraconazole 60% | Sodium sulfate 26%, Leucine 8% | PS80 6% | 130 | 60-175 |
| XXVI | Itraconazole 70% | Sodium sulfate 15%, Leucine 8% | PS80 7% | 130 | 60-175 |
| XXVII | Itraconazole 75% | Sodium sulfate 9.5%, Leucine 8% | PS80 7.5% | 130 | 60-175 |
| XXVIII | Itraconazole 80% | Sodium sulfate 4%, Leucine 8% | PS80 8% | 130 | 60-175 |
| XXIX | Itraconazole 80% | Sodium sulfate 10%, Leucine 2% | PS80 8% | 130 | 60-175 |
| XXX | Itraconazole 80% | Sodium sulfate 11%, Leucine 1% | PS80 8% | 130 | 60-175 |

In a particular aspect, Formulation XII has an FPF less than 5 microns of the total dose of 57%, leading to a fine particle dose less than 5 microns of 2.8 mg for a 10.0 mg total dry powder capsule fill.

The dry powders and/or respirable dry particles described by any of the ranges or specifically disclosed formulations, characterized in the previous paragraph, may be filled into a receptacle, for example a capsule or a blister. When the receptacle is a capsule, the capsule is, for example, a size 2 or a size 3 capsule, and is preferably a size 3 capsule. The capsule material may be, for example, gelatin or HPMC (Hydroxypropyl methylcellulose), and is preferably HPMC.

The dry powder and/or respirable dry particles described and characterized above may be contained in a dry powder inhaler (DPI). The DPI may be a capsule-based DPI or a blister-based DPI, and is preferably a capsule-based DPI. More preferably, the dry powder inhaler is selected from the RS01 family of dry powder inhalers (Plastiape S.p.A., Italy). More preferably, the dry powder inhaler is selected from the RS01 HR or the RS01 UHR2. Most preferably, the dry powder inhaler is the RS01 HR.

Exemplary formulations that may be used in the methods described herein include, but are not limited to, the following:

TABLE 1A

| Formulation | Itraconazole (wt %) | Excipients (wt %) | Polysorbate 80 (PS 80) (wt %) | Itraconazole:PS 80 ratio | Itraconazole subparticle size range (Dv50 nm) |
|---|---|---|---|---|---|
| XXXI | Itraconazole 20.0% | Sodium Sulfate 39.2%, Mannitol 39.2% | PS 80 1.66% | 12:1 | 60-175 |
| XXXII | Itraconazole 50.0% | Sodium Sulfate 22.9%, Mannitol 22.9% | PS 80 4.17% | 12:1 | 60-175 |
| XXXIII | Itraconazole 50.0% | Sodium Sulfate 45.8% | PS 80 4.17% | 12:1 | 60-175 |
| XXXIV | Itraconazole 80.0% | Sodium Sulfate 6.66%, Mannitol 6.67% | PS 80 6.67% | 12:1 | 60-175 |
| XXXV | Itraconazole 80.0% | Sodium Sulfate 13.3% | PS 80 6.67% | 12:1 | 60-175 |
| XXXVI | Itraconazole 92.3% | N/A | PS 80 7.69% | 12:1 | 60-175 |
| XXXVII | Itraconazole 20.0% | Sodium Sulfate 39.5%, Mannitol 39.5% | PS 80 1.00% | 20:1 | 60-175 |
| XXXVIII | Itraconazole 50.0% | Sodium Sulfate 23.8%, Mannitol 23.8% | PS 80 2.50% | 20:1 | 60-175 |
| XXXIX | Itraconazole 80.0% | Sodium Sulfate 8.00%, Mannitol 8.00% | PS 80 4.00% | 20:1 | 60-175 |
| XXXX | Itraconazole 20.0% | Sodium Sulfate 60.9%, Leucine 17.4% | PS 80 1.66% | 12:1 | 60-175 |
| XXXXI | Itraconazole 50.0% | Sodium Sulfate 35.7%, Leucine 10.2% | PS 80 4.16% | 12:1 | 60-175 |

TABLE 1A-continued

| Formulation | Itraconazole (wt %) | Excipients (wt %) | Polysorbate 80 (PS 80) (wt %) | Itraconazole:PS 80 ratio | Itraconazole subparticle size range (Dv50 nm) |
|---|---|---|---|---|---|
| XXXXII | Itraconazole 60.0% | Sodium Sulfate 27.2%, Leucine 7.78% | PS 80 5.00% | 12:1 | 60-175 |
| XXXXIII | Itraconazole 70.0% | Sodium Sulfate 18.8%, Leucine 5.37% | PS 80 5.83% | 12:1 | 60-175 |
| XXXXIV | Itraconazole 80.0% | Sodium Sulfate 10.4%, Leucine 2.96% | PS 80 6.67% | 12:1 | 60-175 |
| XXXXV | Itraconazole 80.0% | Sodium Sulfate 6.67%, Leucine 6.66% | PS 80 6.67% | 12:1 | 60-175 |
| XXXXVI | Itraconazole 80.0% | Sodium Sulfate 2.96%, Leucine 10.4% | PS 80 6.67% | 12:1 | 60-175 |
| XXXXVII | Itraconazole 20.0% | Sodium Sulfate 61.4%, Leucine 17.6% | PS 80 1.00% | 20:1 | 60-175 |
| XXXXVIII | Itraconazole 50.0% | Sodium Sulfate 36.9%, Leucine 10.6% | PS 80 2.50% | 20:1 | 60-175 |
| XLIX | Itraconazole 50.0% | Sodium Sulfate 47.5% | PS 80 2.50% | 20:1 | 60-175 |
| L | Itraconazole 60.0% | Sodium Sulfate 28.8%, Leucine 8.20% | PS 80 3.00% | 20:1 | 60-175 |
| LI | Itraconazole 70.0% | Sodium Sulfate 20.6%, Leucine 5.89% | PS 80 3.50% | 20:1 | 60-175 |
| LII | Itraconazole 80.0% | Sodium Sulfate 12.4%, Leucine 3.56% | PS 80 4.00% | 20:1 | 60-175 |
| LIII | Itraconazole 95.2% | N/A | PS 80 4.76% | 20:1 | 60-175 |
| LIV | Itraconazole 20.0% | Sodium Sulfate 61.7%, Leucine 17.6% | PS 80 0.667% | 30:1 | 60-175 |
| LV | Itraconazole 50.0% | Sodium Sulfate 37.6%, Leucine 10.7% | PS 80 1.67% | 30:1 | 60-175 |
| LVI | Itraconazole 60% | Sodium Sulfate 29.6%, Leucine 8.44% | PS 80 2.00% | 30:1 | 60-175 |
| LVII | Itraconazole 70% | Sodium Sulfate 21.5%, Leucine 6.15% | PS 80 2.33% | 30:1 | 60-175 |
| LVIII | Itraconazole 80% | Sodium Sulfate 13.5%, Leucine 3.85% | PS 80 2.67% | 30:1 | 60-175 |

Methods for Preparing Dry Powders and Dry Particles

The respirable dry particles and dry powders can be prepared using any suitable method, with the proviso that the dry powder formulation cannot be an extemporaneous dispersion. Many suitable methods for preparing dry powders and/or respirable dry particles are conventional in the art, and include single and double emulsion solvent evaporation, spray drying, spray-freeze drying, milling (e.g., jet milling), blending, solvent extraction, solvent evaporation, phase separation, simple and complex coacervation, interfacial polymerization, suitable methods that involve the use of supercritical carbon dioxide ($CO_2$), sonocrystalliztion, nanoparticle aggregate formation and other suitable methods, including combinations thereof. Respirable dry particles can be made using methods for making microspheres or microcapsules known in the art. These methods can be employed under conditions that result in the formation of respirable dry particles with desired aerodynamic properties (e.g., aerodynamic diameter and geometric diameter). If desired, respirable dry particles with desired properties, such as size and density, can be selected using suitable methods, such as sieving.

Suitable methods for selecting respirable dry particles with desired properties, such as size and density, include wet sieving, dry sieving, and aerodynamic classifiers (such as cyclones).

The respirable dry particles are preferably spray dried. Suitable spray-drying techniques are described, for example, by K. Masters in "Spray Drying Handbook", John Wiley & Sons, New York (1984). Generally, during spray-drying, heat from a hot gas such as heated air or nitrogen is used to evaporate a solvent from droplets formed by atomizing a continuous liquid feed. When hot air is used, the moisture in the air is at least partially removed before its use. When nitrogen is used, the nitrogen gas can be run "dry", meaning that no additional water vapor is combined with the gas. If desired the moisture level of the nitrogen or air can be set before the beginning of spray dry run at a fixed value above "dry" nitrogen. If desired, the spray drying or other instruments, e.g., jet milling instrument, used to prepare the dry particles can include an inline geometric particle sizer that determines a geometric diameter of the respirable dry particles as they are being produced, and/or an inline aerodynamic particle sizer that determines the aerodynamic diameter of the respirable dry particles as they are being produced.

For spray drying, solutions, emulsions or suspensions that contain the components of the dry particles to be produced in a suitable solvent (e.g., aqueous solvent, organic solvent, aqueous-organic mixture or emulsion) are distributed to a drying vessel via an atomization device. For example, a nozzle or a rotary atomizer may be used to distribute the solution or suspension to the drying vessel. The nozzle can be a two-fluid nozzle, which can be in an internal mixing setup or an external mixing setup. Alternatively, a rotary atomizer having a 4- or 24-vaned wheel may be used. Examples of suitable spray dryers that can be outfitted with a rotary atomizer and/or a nozzle, include, a Mobile Minor Spray Dryer or the Model PSD-1, both manufactured by GEA Niro, Inc. (Denmark), Büchi B-290 Mini Spray Dryer (BÜCHI Labortechnik AG, Flawil, Switzerland), ProCepT Formatrix R&D spray dryer (ProCepT nv, Zelzate, Belgium), among several other spray dryer options. Actual spray drying conditions will vary depending, in part, on the composition of the spray drying solution or suspension and material flow rates. The person of ordinary skill will be able to determine appropriate conditions based on the compositions of the solution, emulsion or suspension to be spray dried, the desired particle properties and other factors. In general, the inlet temperature to the spray dryer is about 90° C. to about 300° C. The spray dryer outlet temperature will vary depending upon such factors as the feed temperature and the properties of the materials being dried. Generally, the outlet temperature is about 50° C. to about 150° C. If desired, the respirable dry particles that are produced can be fractionated by volumetric size, for example, using a sieve, or fractioned by aerodynamic size, for example, using a cyclone, and/or further separated according to density using techniques known to those of skill in the art.

To prepare the respirable dry particles, generally, an emulsion or suspension that contains the desired components of the dry powder (i.e., a feedstock) is prepared and spray dried under suitable conditions. Preferably, the dissolved or suspended solids concentration in the feedstock is at least about 1 g/L, at least about 2 g/L, at least about 5 g/L, at least about 10 g/L, at least about 15 g/L, at least about 20 g/L, at least about 30 g/L, at least about 40 g/L, at least about 50 g/L, at least about 60 g/L, at least about 70 g/L, at least about 80 g/L, at least about 90 g/L or at least about 100 g/L. The feedstock can be provided by preparing a single solution, suspension or emulsion by dissolving, suspending, or emulsifying suitable components (e.g., salts, excipients, other active ingredients) in a suitable solvent. The solution, emulsion or suspension can be prepared using any suitable methods, such as bulk mixing of dry and/or liquid components or static mixing of liquid components to form a combination. For example, a hydrophilic component (e.g., an aqueous solution) and a hydrophobic component (e.g., an organic solution) can be combined using a static mixer to form a combination. The combination can then be atomized to produce droplets, which are dried to form respirable dry particles. Preferably, the atomizing step is performed immediately after the components are combined in the static mixer. Alternatively, the atomizing step is performed on a bulk mixed solution.

The feedstock can be prepared using any solvent in which the anti-fungal agent in particulate form has low solubility, such as an organic solvent, an aqueous solvent or mixtures thereof. Suitable organic solvents that can be employed include but are not limited to alcohols such as, for example, ethanol, methanol, propanol, isopropanol, butanols, and others. Other organic solvents include but are not limited to tetrahydrofuran (THF), perfluorocarbons, dichloromethane, chloroform, ether, ethyl acetate, methyl tert-butyl ether and others. Co-solvents that can be employed include an aqueous solvent and an organic solvent, such as, but not limited to, the organic solvents as described above. Aqueous solvents include water and buffered solutions. A preferred solvent is water.

Various methods (e.g., static mixing, bulk mixing) can be used for mixing the solutes and solvents to prepare feedstocks, which are known in the art. If desired, other suitable methods of mixing may be used. For example, additional components that cause or facilitate the mixing can be included in the feedstock. For example, carbon dioxide produces fizzing or effervescence and thus can serve to promote physical mixing of the solute and solvents.

The feedstock or components of the feedstock can have any desired pH, viscosity or other properties. If desired, a pH buffer can be added to the solvent or co-solvent or to the formed mixture. Generally, the pH of the mixture ranges from about 3 to about 8.

Dry powder and/or respirable dry particles can be fabricated and then separated, for example, by filtration or centrifugation by means of a cyclone, to provide a particle sample with a preselected size distribution. For example, greater than about 30%, greater than about 40%, greater than about 50%, greater than about 60%, greater than about 70%, greater than about 80%, or greater than about 90% of the respirable dry particles in a sample can have a diameter within a selected range. The selected range within which a certain percentage of the respirable dry particles fall can be, for example, any of the size ranges described herein, such as between about 0.1 to about 3 microns VMGD.

The suspension may be a nano-suspension, similar to an intermediate for making dry powder containing nano-crystalline drug.

The dry powder may be a drug embedded in a matrix material, such as sodium sulfate and leucine. Optionally, the dry powder may be spray dried such that the dry particles are small, dense, and dispersible.

The dry powders can consist solely of the respirable dry particles described herein without other carrier or excipient particles (referred to as "neat powders"). If desired the dry powders can comprise blends of the respirable dry particles described herein and other carrier or excipient particles, such as lactose carrier particles that are greater than 10 microns, 20 microns to 500 microns, and preferably between 25 microns and 250 microns.

In a preferred embodiment, the dry powders do not contain carrier particles. In one aspect, the crystalline drug particles are embedded in a matrix comprising excipient and/or stabilizer. The dry powder may comprise respirable dry particles of uniform content, wherein each particle contains crystalline drug. Thus, as used herein, "uniform content" means that every respirable particle contains some amount of anti-fungal agent in crystalline particulate form, stabilizer, and excipient.

The dry powders can comprise respirable dry particles wherein at least 98%, at least 99%, or substantially all of the particles (by weight) contain an anti-fungal agent.

The dry powders can comprise crystalline drug particles distributed throughout a matrix comprising one or more excipients. The excipients can comprise any number of salts, sugars, lipids, amino acids, surfactants, polymers, or other components suitable for pharmaceutical use. Preferred excipients include sodium sulfate and leucine. The dry powders are typically manufactured by first processing the crystalline drug to adjust the particle size using any number of techniques that are familiar to those of skill in the art (e.g., wet milling, jet milling). The crystalline drug is processed in an antisolvent with a stabilizer to form a suspension. Preferred stabilizers include polysorbate (Tween) 80 and oleic acid. The stabilized suspension of crystalline drug is then spray dried with the one or more additional excipients. The resulting dry particles comprise crystalline drug dispersed throughout an excipient matrix with each dry particle having a homogenous composition.

In a particular embodiment, a dry powder of the present invention is made by starting with crystalline drug (e.g., itraconazole), which is usually obtainable in a micro-crystalline size range. The particle size of the micro-crystalline drug is reduced into the nano-crystalline size using any of a number of techniques familiar to those of skill in the art, including but not limited to, high-pressure homogenization, high-shear homogenization, jet-milling, pin milling, microfluidization, or wet milling (also known as ball milling, pearl milling or bead milling). Wet milling is often preferred, as it is able to achieve a wide range of particle size distributions, including those in the nanometer (<1 μm) size domain. What becomes especially important in the sub-micron size domain is the use of surface stabilizing components, such as surfactants (e.g., Tween 80). Surfactants enable the creation of submicron particles during milling and the formation of physically stable suspensions, as they sequester the many high energy surfaces created during milling preventing aggregation and sedimentation. Thus, the presence of the surfactant is important to spray drying homogenous microparticles as the surfactant allows for the formation of a uniform and stable suspension ensuring compositional homogeneity across particles. The use of surfactant allows for formation of micro-suspension or nano-suspensions. With the surfactant, the nano-crystalline drug (e.g., ITZ) particles are suspended in a stable colloidal suspension in the anti-solvent. The anti-solvent for the drug can utilize water, or a combination of water and other miscible solvents such as alcohols or ketones as the continuous anti-solvent phase for the colloidal suspension. A spray drying feedstock may be prepared by dissolving the soluble components in a desired solvent(s) followed by dispersing the surfactant-stabilized crystalline drug nanosuspension in the resulting feedstock while mixing, although the process is not limited to this specific order of operations.

Methods for analyzing the dry powders and/or respirable dry particles are found in the Exemplification section below.

Liquid Formulations

Liquid formulations for delivery with a pressurized metered dose inhaler (pMDI) or with a soft mist inhaler (SMI) can be prepared using any suitable method. For example, for use with a pMDI, a feedstock may be prepared inside a pressurized canister in which itraconazole in crystalline particulate form is suspended in a propellant such as a HFA propellant or a CFC propellant, optionally stabilized with a stabilizer such as polysorbate 80. The pressurized suspension may then be delivered into the respiratory tract of a patient by actuating the pMDI. Table 2 contains various embodiments for delivery of the itraconazole in crystalline particulate form by use of the pMDI. The nanoparticle solids concentration may vary from about 5%, about 10%, about 15%, about 20%, about 25%, about 30%, about 35%, about 40%, or about 50%. The dose volume of the pMDI may vary from about 20 uL to about 110 uL. The amount of itraconazole in the dose volume may be about 15%, 20%, 25%, 30% or 40%. The remainder of the volume may comprise propellant and optionally a surfactant. The pMDI delivery efficiency may be about 15%, 20%, 25%, 30% or 40%. Nominal doses of itraconazole in a pMDI may be varied from about 0.50 mg to about 12 mg. For example, the nominal dose may be about 2 mg, about 3 mg, about 4 mg, about 5 mg, about 6 mg, about 7 mg, about 8 mg, about 9 mg, about 10 mg or about 12 mg. The calculated delivery dose may range from about 0.1 mg to about 5 mg.

TABLE 2

Pressurized Metered Dose Inhaler (pMDI)

| Nanoparticle solids concentration (%) | Dose volume from pMDI (uL) | Drug amount in dose volume (%) | pMDI delivery efficiency (%) | Nominal dose from pMDI (mg) | Delivered dose from pMDI (mg) |
|---|---|---|---|---|---|
| 10 | 25 | 20 | 30 | 0.50 | 0.15 |
| 10 | 25 | 30 | 20 | 0.75 | 0.15 |
| 10 | 25 | 30 | 30 | 0.75 | 0.23 |
| 10 | 100 | 20 | 30 | 2.00 | 0.60 |
| 10 | 100 | 30 | 20 | 3.00 | 0.60 |
| 10 | 100 | 30 | 30 | 3.00 | 0.90 |
| 25 | 25 | 20 | 30 | 1.25 | 0.38 |
| 25 | 25 | 30 | 20 | 1.88 | 0.38 |
| 25 | 25 | 30 | 30 | 1.88 | 0.56 |
| 25 | 100 | 20 | 30 | 5.00 | 1.50 |
| 25 | 100 | 30 | 20 | 7.50 | 1.50 |
| 25 | 100 | 30 | 30 | 7.50 | 2.25 |
| 35 | 25 | 20 | 30 | 1.75 | 0.53 |
| 35 | 25 | 30 | 20 | 2.63 | 0.53 |
| 35 | 25 | 30 | 30 | 2.63 | 0.79 |
| 35 | 100 | 20 | 30 | 7.00 | 2.10 |
| 35 | 100 | 30 | 20 | 10.50 | 2.10 |
| 35 | 100 | 30 | 30 | 10.50 | 3.15 |

| | |
|---|---|
| density of water: | 1 g/ml |
| Unit conversion: | 1000 mg/g |
| Unit conversion | 1000 uL/mL |

For use with an SMI, for example, a feedstock may be prepared in which itraconazole in crystalline particulate form is suspended in a solvent such as water in which the itraconazole is poorly soluble and stabilized with a stabilizer such as polysorbate 80. The suspension may be stored in a collapsible bag inside a cartridge which is loaded inside the device. A forced metered volume of suspension proceeds through a capillary tube into a micropump. Upon actuation of the SMI, a dose may be delivered to a patient. Table 3 contains various embodiments for delivery of the itraconazole in crystalline particulate form by use of the SMI. The nanoparticle solids concentration vary from about 5%, about 10%, about 15%, about 20%, about 25%, about 30%, about 35%, about 40%, or about 50%. The dose volume of the SMI may vary from about 10 uL to about 25 uL. The formulation may comprise itraconazole in crystalline particulate form and surfactant. The SMI delivery efficiency may be about 65%, 70%, 75%, 80%, or 85%. Nominal doses of itraconazole in a pMDI may vary from about 1.0 mg to about 8 mg. For example, the nominal dose may be about 2 mg, about 3 mg, about 4 mg, about 5 mg, about 6 mg, about 7 mg, or about 8 mg. The calculated delivery dose may range from about 0.5 mg to about 5 mg.

TABLE 3

Soft Mist Inhaler (SMI)

| Nanoparticle solids concentration (%) | Dose volume from SMI (uL) | pMDI delivery efficiency (%) | Nominal dose from pMDI (mg) | Delivered dose from pMDI (mg) |
|---|---|---|---|---|
| 10 | 15 | 75 | 1.50 | 1.13 |
| 25 | 15 | 75 | 3.75 | 2.81 |
| 35 | 15 | 75 | 5.25 | 3.94 |

| | |
|---|---|
| density of water: | 1 g/mL |
| Unit conversion: | 1000 mg/g |
| Unit conversion: | 1000 uL/mL |

EXEMPLIFICATION

Example 1. Human Simulation: Oral Inhalation and Oral Solution Administration Certain assumptions were made for this human simulation. Pulmonary systemic absorption rates estimated using a rat model were used as input in the human simulations. Pulmonary solubility values from the rat model were used as the starting point for human simulations. Particle size distribution using Alberta Idealized Throat (MMAD and GSD) data was used along with ICRP66 model in GastroPlus™ to estimate deposition fraction in humans. An actual dose incorporating approximately 56% deposited in lung and approximately 12.6% in throat was used; the remaining percentage of the drug was assumed to be retained in apparatus.

Single dose pharmacokinetic parameters for Formulation XII was simulated over fourteen days of repeated exposure. A dose proportional increase in both total lung and plasma concentration was predicted from 5 mg to 20 mg. A similar half-life was predicted between lung and plasma.

TABLE 4

| Single Dose PK Parameters | | | | | | |
|---|---|---|---|---|---|---|
| Dose (mg) | $T_{max}$ (h) | $C_{max}$ (ng/ml) | $DNC_{max}$ (ng/mL/mg) | $AUC_t$ (h × ng/mL) | $AUC_{inf}$ (h × ng/mL) | $T_{1/2}$ (h) |
| Plasma Exposure Parameters for Inhaled Dose | | | | | | |
| 5 | 80.7 | 0.275 | 0.0551 | 68.4 | 87.2 | 128 |
| 10 | 81.5 | 0.549 | 0.0549 | 136 | 174 | 128 |
| 20 | 81.9 | 1.09 | 0.0547 | 272 | 347 | 128 |
| Total Lung Exposure Parameters for Inhaled Dose | | | | | | |
| 5 | 0.00 | 2020 | 403 | 199000 | 222000 | 104 |
| 10 | 0.00 | 4030 | 403 | 398000 | 444000 | 104 |
| 20 | 0.00 | 8070 | 403 | 796000 | 888000 | 104 |

AUCinf: area under the concentration-time curve from the time of drug administration (time 0) extrapolated to infinity; AUCt: area under the concentration-time curve from the time of drug administration (time 0) to a specific time (336 hours); Cmax: maximum observed drug concentration; DNCmax: dose normalized Cmax; t1/2: half-life; Tmax: time to maximum observed concentration.

Dose proportional increases in the plasma and lung are predicted after multiple doses. After seven days of dosing, the model predicted accumulation in lung and larger accumulation in the plasma. Based on human predictions, some accumulation of undissolved drug within the alveolar interstitial region with subsequent doses was anticipated. Plasma concentration after oral solution administration was higher than plasma concentrations at either 5- or 20-mg oral inhalation dose levels. However, total lung concentration was higher after oral inhalation administration. As such, total lung:plasma ratio was significantly higher for oral inhalation administration when compared to oral solution administration.

TABLE 5

| Multiple Dose PK Parameters | | | | | | | |
|---|---|---|---|---|---|---|---|
| | Day 1 | | Day 7 | | | | |
| Dose (mg) | $C_{max}$ (ng/mL) | $AUG_t$[a] (h × ng/mL) | $C_{max}$ (ng/mL) | $AUG_t$ (h × ng/mL) | $AUC_{0\text{-}24}$ (h × ng/mL) | AR $C_{max}$ | AR $AUC_{0\text{-}24}$ |
| Plasma Exposure Parameters | | | | | | | |
| 5-mg Inhalation Dose | 0.230 | 4.11 | 1.78 | 409 | 41.3 | 7.71 | 10.1 |
| 20-mg Inhalation Dose | 0.902 | 16.3 | 7.05 | 1630 | 164 | 7.82 | 10.1 |
| Total Lung Exposure Parameters | | | | | | | |
| 5-mg Inhalation Dose | 2010 | 36900 | 7190 | 904000 | 151000 | 3.58 | 4.10 |
| 20-mg Inhalation Dose | 8030 | 148000 | 28800 | 3620000 | 605000 | 3.58 | 4.10 |

[a]$AUC_{0\text{-}t}$ is $AUC_{0\text{-}24}$ for single dose.

Abbreviations: AR: accumulation ratio; $AUC_{0\text{-}24}$: area under the plasma concentration-time curve from time 0 to 24 hours; $AUC_{inf}$: area under the plasma concentration-time curve from the time of drug administration (time 0) extrapolated to infinity; $AUC_t$: area under the concentration-time curve from the time of drug administration (time 0) to a specific time (24 hours for single dose and 360 hours for multiple dose); $C_{max}$: maximum observed drug concentration.

Table 6 show modelled human clinical data with Formulation XII inhaled (oral inhalation) at 5 or 20 mg doses or oral Sporanox (oral solution) at 200 mg, after a single dose. The lung:plasma ratios compare the AUC data in the lung and the plasma over the 7 day period for each dose. The ratios are substantially higher with an inhaled dose than with an oral dose. Even though the oral dose may achieve lung levels that might result in therapeutic lung levels, it would require a greater total dose delivered, as well as greater systemic exposure (you could probably get the same lung exposure with 0.2 mg inhaled as you can with 200 mg orally)

TABLE 6

Oral versus Inhaled Single dose (AUC over 7 days)

| Formulation | Dose (mg) | Dosing interval | Lung AUC0-168 (ng × h/mL) | Plasma AUC0-168 (ng × h/mL) | Lung:Plasma Ratio |
|---|---|---|---|---|---|
| Oral Inhalation | 5 | QD | 151000 | 41.4 | 3650 |
| Oral Inhalation | 20 | QD | 605000 | 164 | 3690 |
| Oral Solution | 200 | QD | 6370 | 2200 | 2.90 |

Table 7 shows exposure over a 24-hour period at 'steady state' on Day 21. Dosing daily via inhalation was compared with possible dosing every other day (EOD) via inhalation. The EOD dosing option appeared to be half the daily dose, so it may be possible to refine the exposure kinetics based on regimen. Even with EOD dosing, the exposure in the lung is significantly higher compared to that seen after 200 mg oral dose daily.

TABLE 7

Oral versus Inhaled Steady State

| Formulation | Dosing Interval | Lung $AUC_{0-24}$ (ng × h/mL) | Plasma $AUC_{0-24}$ (ng × h/mL) | Lung:Plasma Ratio |
|---|---|---|---|---|
| 20-mg Inhalation Dose | QD | 810000 | 281 | 2880 |
| 20-mg Inhalation Dose | EOD | 451000 | 145 | 3110 |
| Standard Oral Solution Dose | QD | 6590 | 2280 | 2.90 |

Abbreviations: $AUC_{0-24}$: area under the plasma concentration-time curve from time 0 to 24 hours; EOD: every other day; QD: once daily.

Figure 1B:
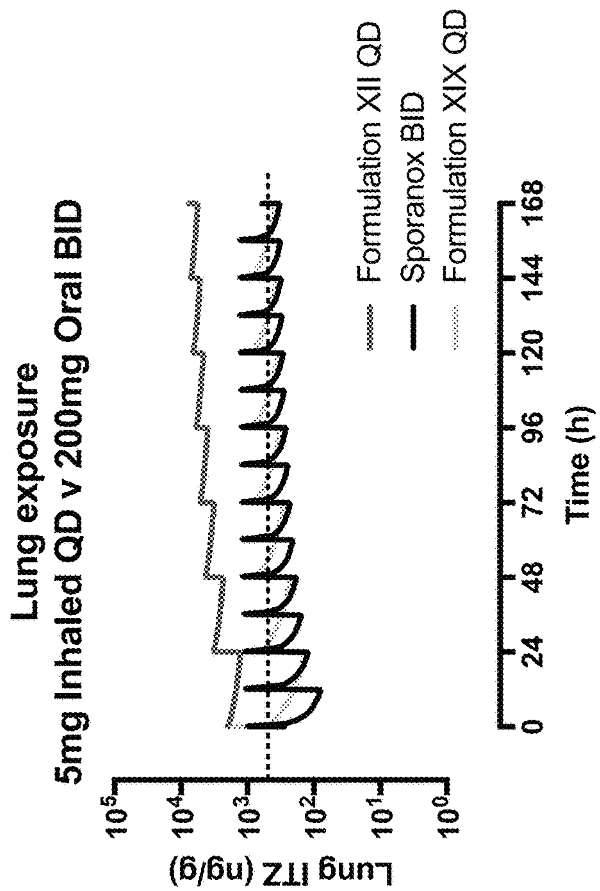

FIGS. 1A and 1B show the kinetics of three anti-fungal formulations at a 5 mg dose. On the left (FIG. 1A), the graph shows plasma exposure with the normal clinical Sporanox twice daily dosing regimen versus once daily Formulation XIX or Formulation XII dosing. Very clearly, the inhaled doses resulted in much lower systemic exposure and the Formulation XII formulation, though it ultimately does reach a similar trough exposure level as Formulation XIX, it does so with lower daily variability and much lower Cmax.

On the right (FIG. 1B) is the lung exposure for the same doses and regimen—the dotted line approximates the *Aspergillus* MIC (~500 ng/g or ng/mL). With oral dosing, the lung levels reach above the MIC, but for only short periods during the twice daily dosing and the majority of the exposure period the exposure is below the 'efficacious' level. A very similar exposure profile in the lung was seen with 5 mg of Formulation XIX and Sporanox. However, the exposure profile, even at the lowest dose of 5 mg Formulation XII, resulted in lung exposure above the MIC and Sporanox for the entire 24 hour period, even on Day 1, and consistently across the 7 days of dosing.

Efficacy of triazole anti-fungal formulations are based on AUC/MIC, meaning the exposure above the MIC, in terms of both total exposure and time, are the critical factors determining efficacy. Clearly, the Formulation XII formulation achieves theoretical exposures much more conducive to efficacy than either the Formulation XIX formulation or oral Sporanox and all with greatly reduced systemic exposure.

Figure 2A:
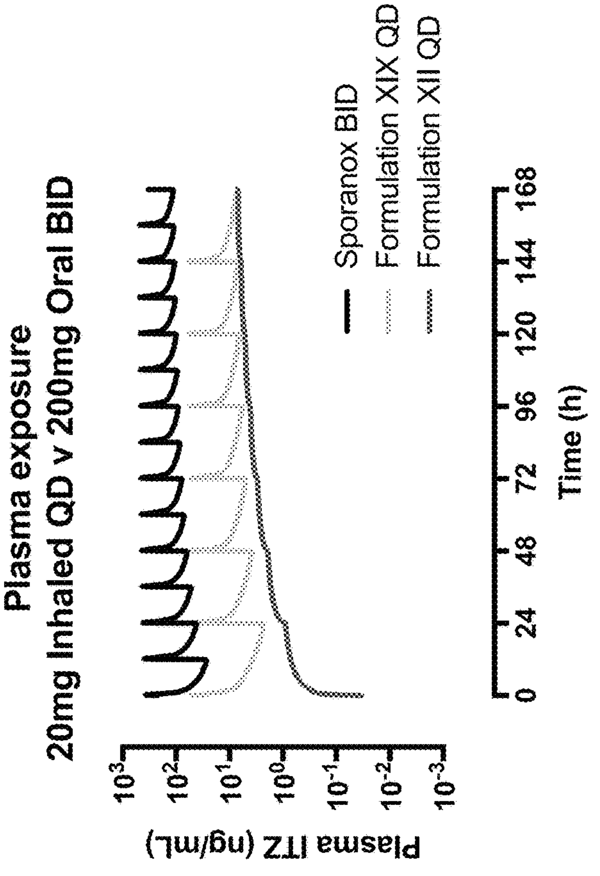
FIGS. 2A and 2B are graphs showing the simulated kinetics of Formulation XIX, Formulation XII, and Sporanox in terms of Plasma Exposure (FIG. 2A) and Lung Exposure (FIG. 2B) using a model established from animal PK data and human data for Sporanox. In both instances simulations 20 mg was inhaled once daily (Formulations XII and XIX), while 200 mg Sporanox oral solution dose was administered twice a day. The concentration of itraconazole was measured over seven days of dosing.
Figure 2B:
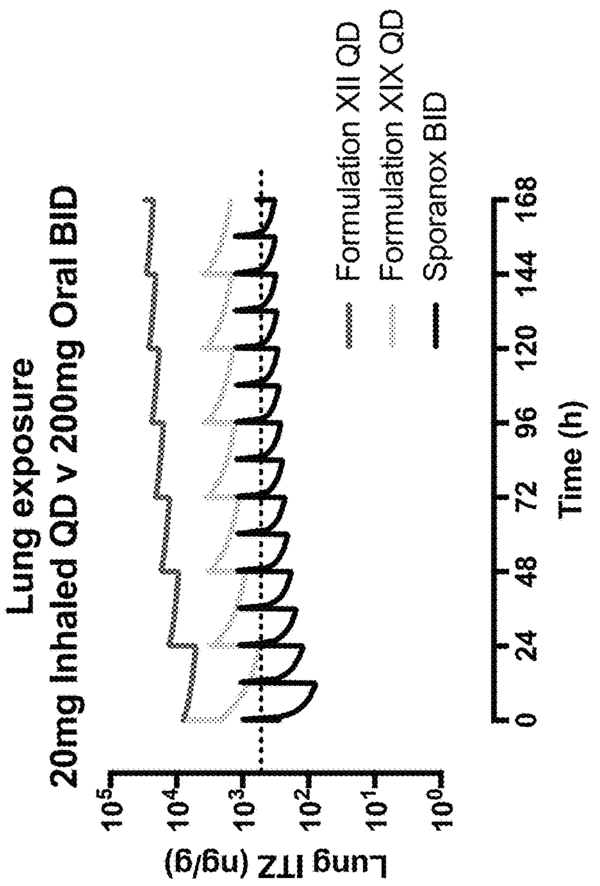

FIG. 2A and FIG. 2B show the kinetics of three anti-fungal formulations at a 20 mg dose. The results and interpretation are similar to the 5 mg inhalation doses described above for FIG. 1A and FIG. 1B, except that a higher dose was administered and the corresponding lung and plasma exposure are increased for the inhaled doses. Using the higher dose, Formulation XIX achieves lung exposure above MIC over a 24 hour period and greater lung exposure than Sporanox. Conversely, the plasma exposure remains significantly below that of Sporanox. The 20 mg exposure of Formulation XII results in higher lung exposure than the 5 mg dose, that remains consistently above the MIC and the exposure of Sporanox throughout the timecourse.

Example 2. Phase 1/1b: Safety-Tolerability Study

A safety, tolerability, and PK study in Healthy Volunteers and Asthmatics highlights the lung and plasma PK advantages over Oral Sporanox. In part 1 of the study, a single ascending dose (5 mg, 10 mg, 25 mg, and 35 mg) of Formulation XII is administered to normal healthy volunteers (n=6/cohort). In part 2 of the study, multiple ascending dose (10 mg, 20 mg) of Formulation XII is administered to healthy volunteers (n=6/cohort), with an optional 3$^{rd}$ cohort receiving up to 35 mg dose. The safety and tolerability of Formulation XII is assessed during the administration of Formulation XII up to 14 days at doses that are expected to provide more than five times higher lung exposure than oral Sporanox, and more than five times lower itraconazole plasma levels than observed with oral Sporanox. 1001661 Part 3 of the study assesses the safety and tolerability of Formulation XII or oral Sporanox administered as a single dose to asthmatics (n=16) in a cross-over design. Patients receiving 200 mg of oral Sporanox in the first period will receive a 20 mg dose of Formulation XII in the second period, while patients receiving 20 mg of Formulation XII in the first period will receive a 200 mg oral dose of Sporanox in the second period. Itraconazole levels in sputum and plasma were measured to assess lung and plasma exposure. This study confirms that lung exposure for the Formulation XII results in lung concentrations that are greater than the minimum inhibitory concentration level (MIC) for *A.*

*fumigatus* and higher than those achieved with oral Sporanox. The plasma exposure of itraconazole following administration of Formulation XII was more than 5X lower than that observed with oral Sporanox dosing.

Example 3: Comparison of Respiratory Tract Findings from Two Rat and Three Dog Studies with Inhalation Exposures to Inhaled Itraconazole Formulations XIX and XII Studies were conducted using inhaled dry powder formulations of itraconazole formulated using spray drying in rats and dogs at two testing facilities. All studies included the same active pharmaceutical ingredient, but the formulation excipients in some cases and, in particular, the physiochemical properties of itraconazole in the particles varied. The studies and their results are summarized below.

Rat Studies

A 28-Day Inhalation Study with Formulation XIX in Rats Followed by a 28-Day Recovery Period Rats were exposed to air, placebo, or itraconazole formulated as Formulation XIX at target doses of 5, 20, or 44 mg/kg/day, with itraconazole being 50% of the formulation concentration, for 28 days. Formulation XIX-related microscopic findings were present in the lungs and bronchi, larynx, and tracheal bifurcation at ≥5 mg/kg/day and in the trachea at ≥20 mg/kg/day. In the lungs and bronchi, minimal to slight granulomatous inflammation was present at itraconazole doses ≥5 mg/kg/day. The granulomatous inflammation was characterized by clusters of macrophages and multinucleated cells within the bronchiolar mucosa, often forming papillary outfoldings of the mucosa in the lumen. Macrophages and multinucleated giant cells frequently contained intracytoplasmic spicules. Alveolar macrophage aggregates were also present in the lungs at an incidence above background in rats dosed at ≥20 mg/kg/day. These macrophages were vacuolated, which gave the cytoplasm a foamy appearance.

In the larynx and tracheal bifurcation, minimal to slight granulomatous inflammation was present at itraconazole doses ≥5 mg/kg/day. As in the lung, this inflammation was characterized by clusters of macrophages and multinucleated giant cells with intracytoplasmic spicules within the mucosa. Similar minimal granulomatous inflammation was present in the tracheal mucosa of rats dosed at ≥20 mg/kg/day.

At the end of the 28-day recovery period, bronchiolar granulomatous inflammation was still present in rats dosed at 44 mg/kg/day; thus, the bronchiolar finding at this dose did not resolve during the recovery period. Granulomatous inflammation was not observed in the larynx, tracheal bifurcation, or trachea at the end of the recovery period, suggesting complete resolution in these tissues during the recovery period.

In summary, the main Formulation XIX-related finding was granulomatous inflammation characterized by mucosal macrophages and multinucleated giant cells with cytoplasmic spicules. This finding, which occurred in rats dosed at ≥5 mg/kg/day itraconazole was considered adverse at all doses because it occurred throughout the conducting airways from larynx to small bronchioles and did not resolve in the bronchioles during the recovery period in rats dosed at 44 mg/kg/day (other dose groups not examined at the end of the recovery period). Aggregates of alveolar macrophage with foamy cytoplasm were also present in the lungs at an incidence above background in rats dosed at ≥20 mg/kg/day at the terminal sacrifice.

A 28-Day Inhalation Study with Formulation XII or Formulation XV in Rats

Rats were exposed to itraconazole formulated as Formulation XII at target doses of 5, 15, or 40 mg/kg/day or to Formulation XV at doses of 5 or 15 mg/kg/day for 28 days. In both cases, the itraconazole was 50% of the total formulation concentration. In addition, one group of rats was dosed at 15 mg/kg itraconazole as Formulation XII every three days. Formulation XII and Formulation XV-related minimal to mild accumulations of foamy macrophages were present in the lungs at 15 mg/kg/day with a higher incidence and severity in rats dosed with Formulation XII at 40 mg/kg/day. There may have been a minimal accumulation of foamy macrophages in the lung at 5 mg/kg/day Formulation XII or Formulation XV or 15 mg/k Formulation XII dosed every 3 days, but due to the lack of air or placebo control rats, it was not possible to determine if there was a test item-related effect at these doses. Mild subacute inflammation, which was considered test item related and adverse, was present in rats dosed at 40 mg/kg/day Formulation XII. It was not clear whether minimal subacute inflammation, which occurred in rats dosed at 15 mg/kg/day with Formulation XII or Formulation XV, was test item related. There was no clear difference in the incidence and severity of macrophage accumulation or subacute inflammation between male rats dosed with Formulation XII and Formulation XV at comparable dose levels. There was a suggestion of a higher severity and/or incidence of these findings in female rats dosed at 15 mg/kg/day with Formulation XV compared with Formulation XII.

Dog Studies

A 7-Day Inhalation Study of Formulation XIX in Dogs with a 14-Day Recovery Period Dogs were exposed to itraconazole formulated as Formulation XIX at target doses of 5, 10, or 20 mg/kg/day for 7 days. The itraconazole formulation concentration was 50% of the total. A 14-day recovery group was included for dogs that were exposed at 5 mg/kg/day. Minimal to mild Formulation XIX-related acute inflammation, which was considered adverse, was present in both dogs (one male; one female) dosed at 20 mg/kg/day and minimal acute inflammation was present in the female dog dosed at 10 mg/kg/day. The acute inflammation was characterized by the presence of neutrophils, macrophages, and a few multinucleated giant cells that appeared to contain spicules in their cytoplasm (observed in a post-study slide review). Thus, the acute inflammation exhibited features of granulomatous inflammation. There were no test item-related findings in dogs dosed at 5 mg/kg/day at the terminal or recovery sacrifices.

A 28-Day Inhalation Study of Formulation XIX in Dogs with a 28-Day Recovery Period Dogs were exposed to air, placebo, or itraconazole formulated at target doses of 5, 10, or 20 mg/kg/day for 28 days. The itraconazole formulation concentration was 50% of the total. Minimal to mild, Formulation XIX-related, bronchiolar/peribronchiolar granulomatous inflammation was present in males and females at ≥5 mg/kg/day. Incidence and severity of this finding increased with dose in males at ≥5 mg/kg/day and females at 20 mg/kg/day. The granulomatous inflammation was within and surrounding terminal and respiratory bronchioles and was characterized by aggregates of macrophages and multinucleated giant cells with abundant, eosinophilic cytoplasm. Mild granulomatous inflammation, which occurred at ≥10 mg/kg/day was considered adverse. Granulomatous inflammation completely resolved during the recovery period.

A 14-Day Inhalation Study of Formulation XII and Formulation XV in Dogs

Dogs were exposed to placebo or to itraconazole formulated as Formulation XII at target doses of 2, 6, or 20 mg/kg/day or Formulation XV at target doses of 6 or 20 mg/kg/day for 14 days. In addition, one group of dogs was dosed at a target dose of 6 mg/kg itraconazole as Formulation XII every three days. The itraconazole formulation concentration was 50% of the total in all cases. Test item-related respiratory tract findings were present in dogs administered 20 mg/kg/day Formulation XII or Formulation XV. Test item-related, mild, intra-alveolar, mixed cell inflammation was present in all dogs dosed with 20 mg/kg/day Formulation XII. Test item-related, mild carinal and tracheal mucosal lymphocytic inflammation was present in 2 of 3 dogs dosed with 20 mg/kg/day FORMULATION XII-02C. In additional, minimal, intra-alveolar, mixed cell inflammation was present in 1 of 3 dogs dosed with 20 mg/kg/day Formulation XV. Therefore, the location of findings varied somewhat between Formulation XII and Formulation XV. The variability complicates comparison of Formulation XII to Formulation XV, although the dose level at which clearly test item-related findings occurred (20 mg/kg/day) was the same for both test items. Mild mixed cell inflammation was present in 1 of 3 dogs dosed with 6 mg/kg Formulation XII every three days and 1 of 3 dogs dosed with 6 mg/kg/day Formulation XV. Due to the low incidence of this finding in each of these groups and the lack of findings in other areas of the respiratory tract at these doses, the relationship of inhalation of Formulation XII or Formulation XV was unclear.

Comparison of Formulation XIX to Formulation XII and Formulation XV in Rat Studies Formulation XIX-related findings in the respiratory tract of rats had a different character from those induced by Formulation XII and Formulation XV. In addition, Formulation XIX-related findings involved more regions (tissues) in the respiratory tract and likely were adverse at a lower dose. Recovery was not evaluated in the rat studies with Formulation XII or Formulation XV. However, based on experience with other inhaled materials, it is likely that granulomatous inflammation within the bronchiolar mucosa, which was present after exposure to Formulation XIX, would resolve more slowly than increased alveolar macrophages or subacute inflammation included by Formulation XII or Formulation XV.

Granulomas or granulomatous inflammation composed of macrophages and multinucleated giant cells are common responses to materials that are not readily solubilized within cytoplasmic lysosomes, including aspirated foreign bodies. The presence of these cells in the mucosa at multiple levels in the respiratory tract after inhalation of Formulation XIX suggests that test item impacted and either a) penetrated the epithelium and was phagocytosed by macrophages, or b) dissolved, penetrated the epithelium, and recrystallized, in the interstitium where it was phagocytosed by macrophages, or b) dissolved, penetrated the epithelium, and recrystallized, in the interstitium where it was phagocytosed by macrophages. The lack of complete resolution during the recovery period is not unexpected for a material in a poorly soluble form.

Formulation XII dosed at 40 mg/kg/day exposure resulted in mild subacute inflammation, which was considered test item related and adverse. This subacute inflammation occurred in the alveolar parenchyma and was morphologically different from the granulomatous mucosal inflammation that occurred with Formulation XIX exposure. It was not clear whether minimal subacute inflammation, which occurred in rats dosed at 15 m/kg/day with Formulation XII or Formulation XV, was test item related. In comparing Formulation XII to Formulation XV, there was no clear difference in the incidence and severity of macrophage accumulation or subacute inflammation among male rats dosed with these test items at comparable dose levels. There was a suggestion of a higher severity and/or incidence of these findings in female rats dosed at 15 mg/kg/day with Formulation XV compared with Formulation XII. Recovery was not investigated in the studies with Formulation XII or Formulation XV. However, minimal to mild subacute inflammation and minimal to mild macrophage accumulation are considered reversible findings and would generally be expected to resolve in a 28-day recovery period.

It is difficult to compare alveolar macrophage accumulation across these rat studies because the Formulation XII or Formulation XV study did not include air or placebo controls. Different groups of rats at different testing facilities can have different background incidences of minimal alveolar macrophage accumulation. However, the data from these studies suggest that minimal to mild alveolar macrophage accumulation may have occurred at higher incidences and/or lower doses in rats dosed with Formulation XII or Formulation XV, perhaps indicating greater dispersal in the alveoli of Formulation XII or Formulation XV in a form that was phagocytosed by macrophages.

Comparison of Formulation XIX to Formulation XII and Formulation XV in Dog Studies Formulation XIX-related findings in the respiratory tract of dogs had a different character from those induced by Formulation XII and Formulation XV.

Formulation XIX-related acute inflammation, which was considered adverse, was present in the 7-day dog study at 10 mg/kg/day. There were no Formulation XIX-related findings at 5 mg/kg/day in the 7-day study. Formulation XIX-related granulomatous inflammation was present at ≥5 mg/kg/day in the 28-day dog study and it reached a mild severity where it was considered adverse at ≥10 mg/kg/day. Retrospectively, the acute inflammation observed in the 7-day study could be described as acute, granulomatous inflammation. Thus, the findings were similar across the two dog studies with Formulation XIX, but with differences reflecting the length of the studies. In both studies, the findings were considered adverse at 10 mg/kg/day. The location of the inflammation was primarily bronchiolar/peribronchiolar, as opposed to within alveoli. This location indicates a conducting airway orientation and thus it is somewhat similar to the location of the Formulation XIX-related finding in rats, although it did not exhibit the mucosal location and was not as discreet as the rat finding. Granulomatous inflammation was similar, but not morphologically identical in the rat and dog.

Formulation XII or Formulation XV induced test item-related findings at 20 mg/kg/day in the 14-day dog study. Test item-related, mild, intra-alveolar, mixed cell inflammation was present in all dogs dosed with 20 mg/kg/day Formulation XII. Adversity was not addressed in the 14-day study report, but mild mixed cell inflammation would likely be considered adverse. Findings at 6 mg/kg/day were not clearly test item related due to the low incidence. Dogs were not exposed to Formulation XII or Formulation XV at 10 mg/kg/day, so a direct comparison to Formulation XIX, which was adverse at 10 mg/kg/day cannot be made. However, it might be more appropriate to compare lung tissue levels as opposed to doses when comparing adversity after inhalation exposure and these were substantially higher in animals dosed with Formulation XII and Formulation XV formulations. Granulomatous inflammation associated with Formulation XIX completely resolved during the 28-day recovery period. The 14-day dog study with Formulation XII and Formulation XV did not include a recovery period. Formulation XII or Formulation XV-related mixed cell inflammation in the dog was morphologically somewhat similar to Formulation XII or Formulation XV-related sub-acute inflammation in the rat in that it involved the alveoli and was not granulomatous.

Example 4: Phase 1 Open-Label Study to Assess Safety, Tolerabilty and Pharmacokinetics of Single and Multiple Doses of Itraconazole Administered as a Dry Powder for Inhalation in Healthy Subjects Clinical Pharmacokinetics of Itraconazole Oral Solution Based on Historical Data Itraconazole is metabolized in liver by the cytochrome P450 3A4 isoenzyme system to the major metabolize hydroxy-itraconazole. Hydroxy-itraconazole is active and has anti-fungal activity against many clinically important fungi. Itraconazole is highly bound by plasma protein, 99.8% and 99.6%, oral solution and capsules, respectively.

The pharmacokinetics of oral itraconazole have been studied in both single and multiple dose studies in humans. The pharmacokinetics differ between the two presentations (solution and capsules), with higher exposure observed with the oral solution. It is recommended that the oral solution and capsules not be used interchangeably.

The absolute bioavailability of the oral solution is 55% in healthy volunteers, and increases by 30% when taken under fasted conditions. Under fasted conditions, the steady-state $AUC_{0\text{-}24h}$ is 131±30% of the exposure under fed conditions and it is recommended that the oral solution be administered fasted. At steady-state, under fasted conditions the mean $C_{max}$, $t_{max}$ and $AUC_{0\text{-}24h}$ of a 200 mg daily dose of itraconazole was 1,963±601 ng/mL, 2.5±0.8 h and 29,271±10,285 ng·h/mL, respectively. The half-life of itraconazole at steady state was 39.7±13 h.

Pharmacokinetic Data from Part 1, SAD in Healthy Volunteers

Figure 3:
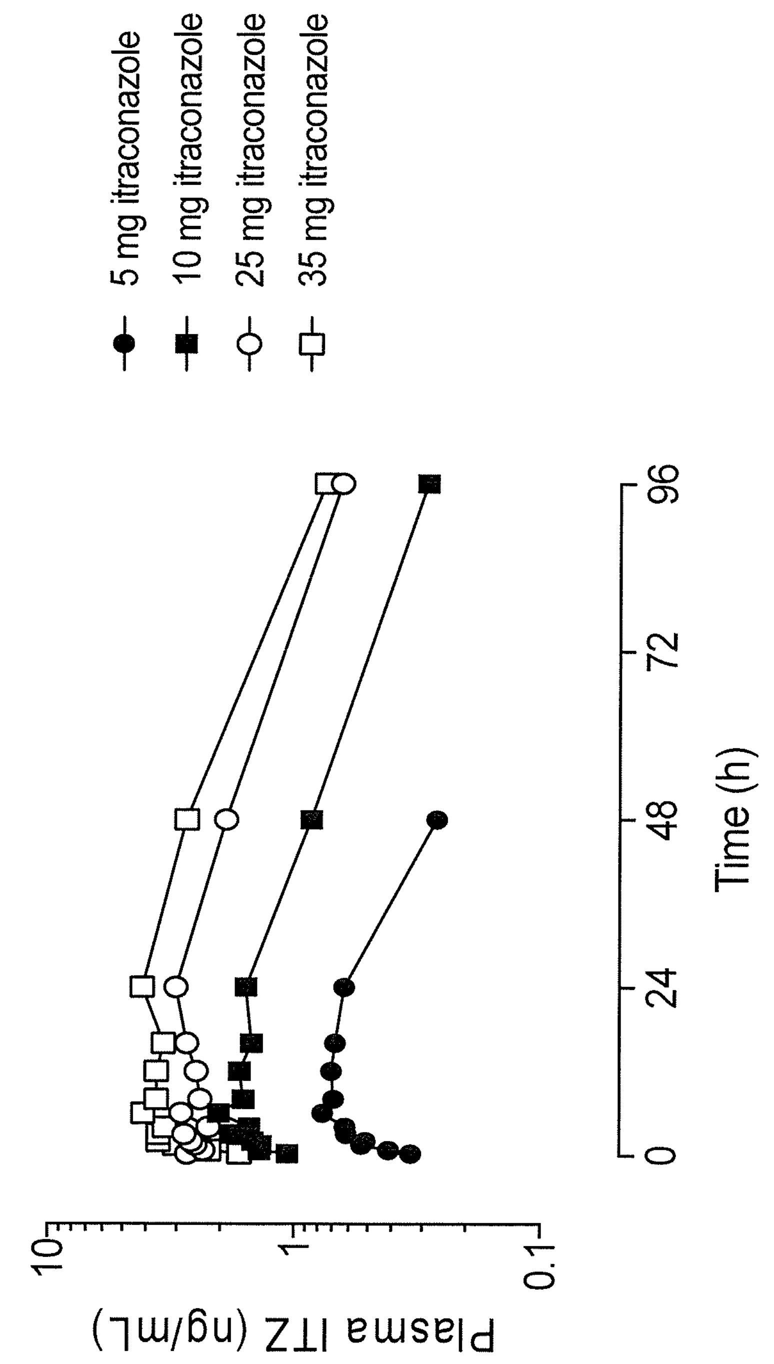
FIG. 3 is a graph showing the Single Dose Formulation XII plasma pharmacokinetic profile over 96 hours in healthy volunteers. Details of the study are provided in Example 4.

Preliminary summary data for systemic pharmacokinetics after a single inhaled dose of Formulation XII are summarized in Table 8 and concentration-time profiles are shown in FIG. 3. The pharmacokinetic data is important because of the effect it has on the safety profile of Formulation XII compared to oral dosing. The data confirms that inhaled dosing with Formulation XII results in low systemic exposure. Doses ranged from 5 mg to 35 mg of itraconazole. Itraconazole was rapidly absorbed into the systemic circulation, with all subjects having detectable plasma exposure at the earliest sampling timepoint of 15 minutes. Exposure was generally maintained during the first 18-24 hours indicating a prolonged absorption. Beyond 24 hours after dosing, plasma concentrations generally declined in a steady mono-exponential manner with the rate of decay similar across all cohorts (range $K_{el}$ geometric means; 0.021-0.032 l/h). Exposure ($C_{max}$ and AUC) increased monotonically and were generally less than dose-proportional.

TABLE 8

Pharmacokinetic data following single, inhaled doses of Formulation XII in healthy volunteers

| Nominal Itraconazole Dose (mg) | $AUC_{0\text{-}24\,h}$ (h · ng/mL) | $AUC_{0\text{-}last}$ (h · ng/mL) | $AUC_{0\text{-}inf}$ (h · ng/mL) | $C_{max}$ (ng/mL) | $t_{max}$* (h) |
|---|---|---|---|---|---|
| 5 | 15.9 | 26.1 | 30.2[a] | 0.87 | 6 |
| 10 | 38.8 | 93.5 | 110.4[b] | 2.28 | 6 |
| 25 | 64.64 | 179.4 | 211.3 | 3.9 | 3 |
| 35 | 86.76 | 224.5 | 182.7[c] | 4.58 | 18 |

Data shown are the geometric mean values for each cohort (n = 5 for the 5 mg dose; n = 6 for the 10, 25 and 35 mg doses).
*median values.

Pharmacokinetic Data from Part 2, MAD in Healthy Volunteers

Figure 4:
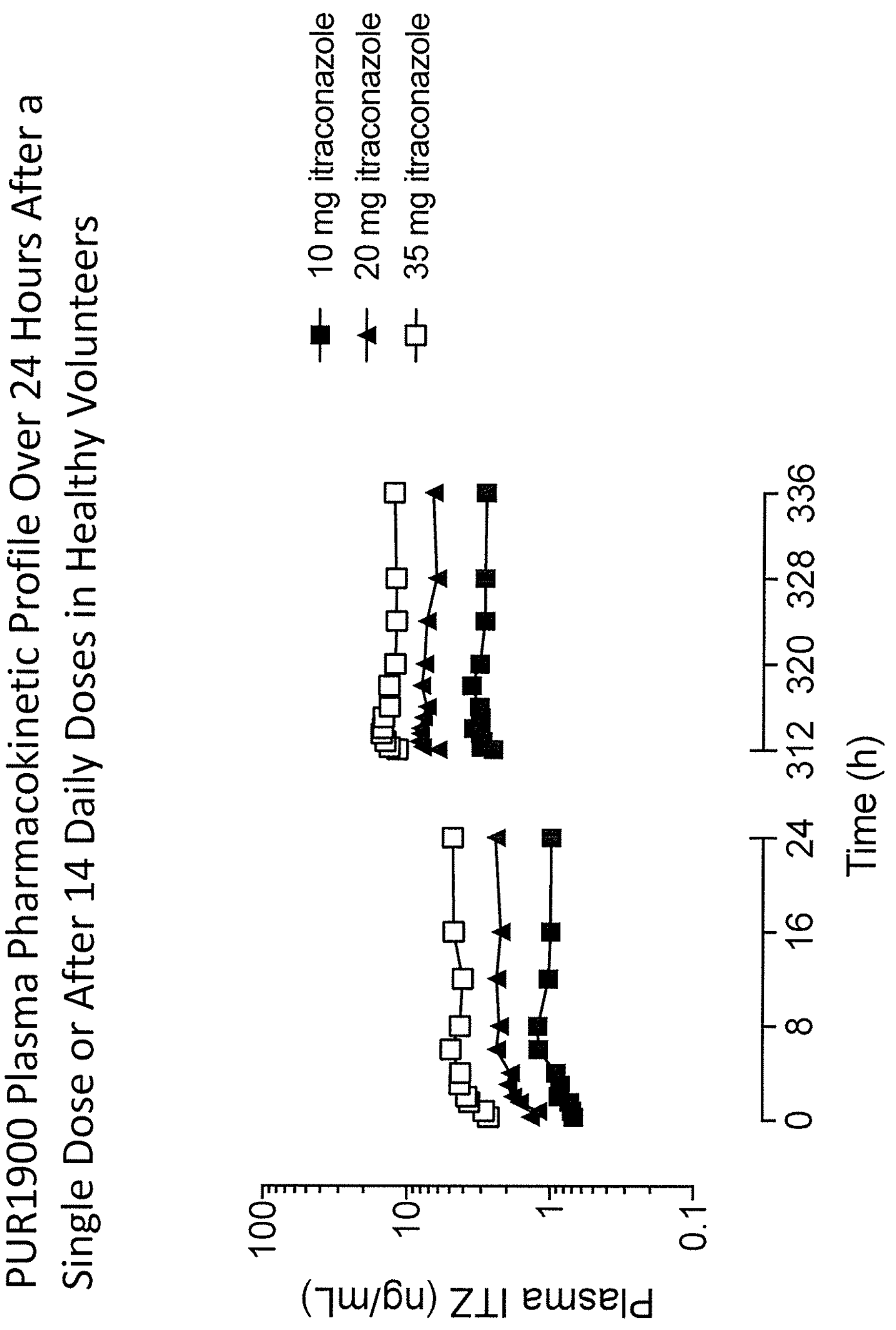
FIG. 4 is a graph showing the Formulation XII plasma pharmacokinetic profile over 24 hours after a single dose or after 14 daily doses in healthy volunteers. Details of the study are provided in Example 4.

Summary data for systemic pharmacokinetics after a single inhaled dose and 14 days of daily inhalation of Formulation XII are summarized in Table 9 and concentration-time profiles are shown in FIG. 4. Doses were either 10 mg, 20 mg or 35 mg of itraconazole. As in Part 1, itraconazole was rapidly absorbed into the systemic circulation with all subjects having detectable plasma exposure at the earliest sampling timepoint of 15 minutes. Exposure was generally maintained during the first 18-24 hours with median $T_{max}$ estimates between 7 hours and 18 hours across cohorts.

Median plasma concentration increased with each repeat dose, with concentrations close to steady state by Day 14. Compared to steady-state plasma levels of itraconazole reported after dosing with the oral solution, exposure following inhalation was 100- to 400-fold lower based on $AUC_{0\text{-}24h}$. Between Day 1 and Day 14 itraconazole accumulation was approximately 3-fold for both $C_{max}$ and $AUC_{0\text{-}24h}$ and similar for each dose. As in Part 1, at the end of dosing, plasma concentrations declined in a steady mono-exponential manner suggesting the absence of any exaggerated lung accumulation that would result in a prolonged systemic exposure.

TABLE 9

Pharmacokinetic data following single and multiple, inhaled doses of Formulation XII in healthy volunteers

| Nominal | DAY 1 | | | DAY 14 | | | | |
|---|---|---|---|---|---|---|---|---|
| Itraconazole | $AUC_{0\text{-}24\,h}$ | $C_{max}$ | $t_{max}$* | $AUC_{0\text{-}24\,h}$ | $C_{max}$ | $t_{max}$* | Accumulation | |
| Dose (mg) | (h · ng/mL) | (ng/mL) | (h) | (h · ng/mL) | (ng/mL) | (h) | $AUC_{0\text{-}24\,h}$ | $C_{max}$ |
| 10 | 24.4 | 1.29 | 7 | 73.2 | 3.77 | 5 | 3.0 | 2.9 |
| 20 | 53.0 | 2.64 | 18 | 174.4 | 8.98 | 4 | 3.3 | 3.4 |
| 35 | 102.4 | 5.23 | 7 | 276.5 | 15.2 | 0.8 | 2.7 | 2.9 |

Data shown are the geometric mean values for each cohort (n = 6 for the 10 mg and 20 mg dose; n = 6 for day 1 and n = 5 for day 14 for the 35 mg dose).
*median values.

Figure 5A:
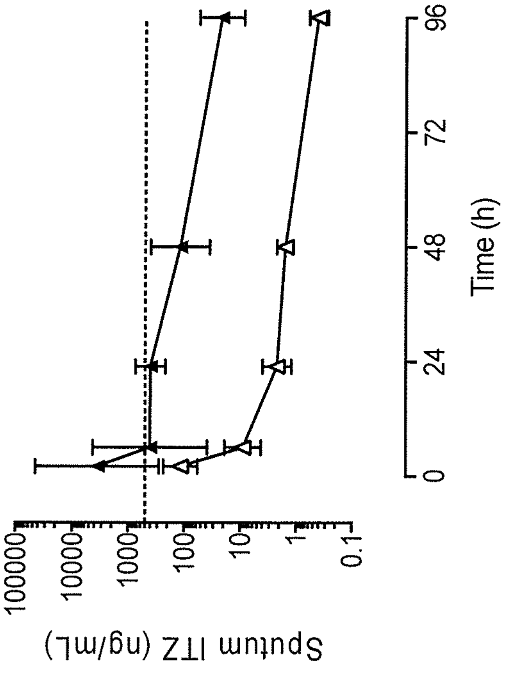
FIGS. 5A and 5B are graphs showing summary data for systemic pharmacokinetics after a single inhaled or oral dose in asthma patients. Pharmacokinetic profiles of Itraconazole in sputum (FIG. 5A) and plasma (FIG. 5B) following single doses of PUR1900 (▲) or oral Sporanox (Δ) administered to asthmatics.
Figure 5B:
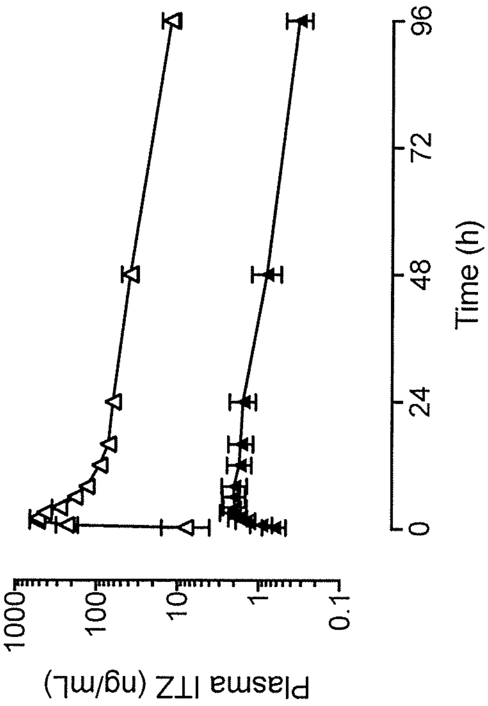

Pharmacokinetic Data from Part 3, Single Doses in Adult Subjects with Mild-to-Moderate Stable Asthma Summary data for systemic pharmacokinetics after a single inhaled or oral dose in asthma patients are summarized in Table 10 and concentration time-profiles are shown in FIG. 5A and FIG. 5B. Doses were either 20 mg itraconazole inhaled as Formulation XII or 200 mg of itraconazole administered as Sporanox oral solution. For both oral and inhaled doses, itraconazole was quickly absorbed into the systemic circulation with median $T_{max}$ estimates of 4.0 hours and 1.5 hours for Formulation XII and Sporanox respectively. Following Formulation XII administration, itraconazole plasma exposure generally increased and/or was maintained over the first 24 hours indicating a prolonged absorption. In contrast, orally administered itraconazole was rapidly absorbed and eliminated, such that exposure peaked soon after dosing, but rapidly declined to levels that are 17% of $C_{max}$ 12 hours after dosing. Total systemic exposure over 24 hours ($AUC_{0\text{-}24h}$), was approximately 85-fold lower after Formulation XII relative to exposure after oral dosing and maximum exposure (Cmax), was approximately 250-fold lower after Formulation XII relative to exposure after oral dosing.

TABLE 10

Pharmacokinetic data following single doses of Formulation XII or oral Sporanox in asthma patients

| | Nominal Dose (mg) | $AUC_{0\text{-}24\,h}$ (h · ng/mL) | $AUC_{0\text{-}last}$ (h · ng/mL) | $AUC_{0\text{-}inf}$ (h · ng/mL) | $C_{max}$ (ng/mL) | $t_{max}$* (h) |
|---|---|---|---|---|---|---|
| Formulation XII | 20 | 41.8 | 90.5 | 105.2 | 2.33 | 4 |
| Sporanox | 200 | 3618 | 6118 | 6649 | 581 | 1.5 |

Data shown are the geometric mean values for each cohort (n = 14 for Formulation XII and n = 15 for Sporanox).
*median values.

Induced sputum was collected 2 hours, 6 hours, and 24 hours after dosing and used to measure itraconazole concentrations using a validated liquid chromatography-mass spectrometry/mass spectrometry (LC-MS/MS) method with a LLOQ (lower limits of quantification) of 0.1 ng/mL. Sputum itraconazole levels were higher with Formulation XII dosing relative to oral Sporanox dosing, with a geometric mean $C_{max}$ after inhalation of 5381 ng/mL compared to a $C_{max}$ of 116.3 ng/mL after oral dosing (FIG. 5A). High lung exposure following Formulation XII was maintained over a 24 hour period, whereas sputum concentrations of itraconazole decreased between 2 hours and 6 hours after a single 200 mg oral itraconazole dose. These data confirm that inhaled dosing with Formulation XII results in high and sustained lung exposure, higher than what is achieved with oral dosing, while maintaining low systemic exposure. Based on geometric mean $C_{max}$ data in lung and plasma, Formulation XII resulted in a lung:ratio of approximately 2300:1 and oral dosing resulted in a lung:plasma ratio of 1:5.

The invention claimed is:

1. A method for treating allergic bronchopulmonary aspergillosis (ABPA) comprising administering via inhalation to the respiratory tract of a patient in need thereof a dry powder comprising:

(i) an anti-fungal agent, wherein the anti-fungal agent is itraconazole in crystalline form and is in an amount of 50% by weight and the itraconazole is in the form of a sub-particle with a volumetric median geometric diameter (VMGD) of 60 nm to 175 nm;

(ii) polysorbate 80 in an amount of 5% by weight;

(iii) sodium sulfate in an amount of 35% by weight; and (iv) leucine in an amount of 10% by weight, wherein said anti-fungal agent is administered in an amount sufficient to achieve concurrently:

a) a lung concentration of anti-fungal agent of between about 500 ng/g or ng/ml and 8100 ng/g or ng/ml; and b) a plasma concentration of anti-fungal agent of between about 0.2 ng/ml and about 25 ng/mL;

wherein the lung and plasma concentrations are achieved for 24 hours following administration of the anti-fungal agent, wherein the itraconazole is administered in a single dose or in an initial dose followed by one or more subsequent doses, wherein each of said doses independently comprises 5 mg to 35 mg nominal dose of itraconazole.

2. The method of claim 1, wherein said patient has cystic fibrosis, asthma and/or is immunocompromised.

3. The method of claim 1, wherein a lung: plasma ratio of at least 100:1 is achieved.

4. The method of claim 1, wherein the itraconazole is administered in the single dose.

5. The method of claim 1, wherein the itraconazole is administered in the initial dose followed by the one or more subsequent doses.

6. The method of claim 1, wherein the single dose or each of the initial dose and the one or more subsequent doses achieves a minimum fungicidal concentration (MFC90) in the lung for at least 24 hours.

7. The method of claim 6, wherein said MFC90 is at least 2000 ng/g or ng/mL.

8. The method of claim 1, wherein the itraconazole is administered once daily.

9. The method of claim 1, wherein the itraconazole is administered once every other day.

10. The method of claim 1, wherein the itraconazole is administered once every three days.

11. The method of claim 1, comprising administering the initial dose of the dry powder to achieve a fungicidal concentration of itraconazole in the lung, followed by administering one or more subsequent doses to maintain a fungistatic concentration of itraconazole in the lung.

12. The method of claim 11, wherein the one or more subsequent doses are administered less frequently than the initial dose.

13. The method of claim 11, wherein each of the one or more subsequent doses is less than the initial dose.

14. The method of claim 1, wherein the itraconazole is administered in one or more doses until steady state lung concentration is achieved.

15. The method of claim 1, wherein the dry powder is administered using a passive dry powder inhaler.

16. The method of claim 2, wherein the patient has cystic fibrosis, has asthma, or is immunocompromised.

17. The method of claim 1, wherein the itraconazole is administered for up to six months.

18. A method for treating allergic bronchopulmonary aspergillosis (ABPA) comprising administering via inhalation to the respiratory tract of a patient in need thereof a dry powder comprising:

(i) an anti-fungal agent, wherein the anti-fungal agent is itraconazole in crystalline form and is in an amount of 50% by weight and the itraconazole is in the form of a sub-particle with a volumetric median geometric diameter (VMGD) of 60 nm to 175 nm;

(ii) polysorbate 80 in an amount of 5% by weight;

(iii) sodium sulfate in an amount of 37% by weight; and (iv) leucine in an amount of 8% by weight, wherein said anti-fungal agent is administered in an amount sufficient to achieve concurrently:

a) a lung concentration of anti-fungal agent of between about 500 ng/g or ng/ml and 8100 ng/g or ng/mL; and b) a plasma concentration of anti-fungal agent of between about 0.2 ng/ml and about 25 ng/ml;

wherein the lung and plasma concentrations are achieved for 24 hours following administration of the anti-fungal agent, wherein the itraconazole is administered in a single dose or in an initial dose followed by one or more subsequent doses, wherein each of said doses independently comprises 5 mg to 35 mg nominal dose of itraconazole.

19. The method of claim 18, wherein the sodium sulfate is sodium sulfate anhydrous.

20. The method of claim 18, wherein the leucine is L-leucine.

* * * * *